United States Patent [19]
Raines et al.

[11] Patent Number: 6,152,881
[45] Date of Patent: Nov. 28, 2000

[54] CALIBRATED MEASUREMENT OF BLOOD VESSELS AND ENDOTHELIUM AFTER REACTIVE HYPEREMIA AND METHOD THEREFOR

[75] Inventors: Jeffrey K. Raines, Coral Gables, Fla.; William Insull, Jr., Houston, Tex.

[73] Assignee: Vasocor, Inc., Miami, Fla.

[21] Appl. No.: 09/277,914

[22] Filed: Mar. 29, 1999

[51] Int. Cl.$^7$ .................................................. A61B 5/02
[52] U.S. Cl. ........................................ 600/507; 600/504
[58] Field of Search ................................. 600/504, 485, 600/490, 500, 507, 481

[56] References Cited

U.S. PATENT DOCUMENTS

| | | | |
|---|---|---|---|
| 4,112,491 | 9/1978 | Bugay | 600/502 |
| 4,590,948 | 5/1986 | Nilsson | 600/479 |
| 4,718,428 | 1/1988 | Russell | 600/492 |
| 5,417,220 | 5/1995 | Apple | 600/500 |
| 5,447,163 | 9/1995 | Apple | 600/500 |
| 5,630,424 | 5/1997 | Raines et al. | 600/507 |
| 5,718,232 | 2/1998 | Raines et al. | 600/507 |

OTHER PUBLICATIONS

Noninvasive assessment of endothelium–dependent flow–mediated dilation of the brachial artery, by A. Uehata et al; Vascular Medicine 2, pp. 87–92, 1997.

Flow–Induced Vasodilation of the Human Brachial Artery is Impaired in Patient [over] 40 years of Age with Coronary Artery Disease, by E. Lieberman, et al., American Journal of Cardiology, 78, pp. 1210–1214, 1996.

Reproducibility of brachial ultrasonography and flow–mediated dilation (FMD) for assessing endothelial function, by K.L. Hardie, et al., Australian New Zealand Journal of Medicine, 27, pp. 649–652, 1997.

Flow–mediated, endothelium–dependent dilation of the brachial arteries is impaired in patients with coronary spastic angina, by T. Motoyama, et al., American Heart Journal, vol. 133, No. 3, pp. 263–267, Mar., 1997.

Non–invasive investigation of endothelium–dependent dilation of the brachial artery in women with primary Raynaud's phenomenon, by A. Ringqvist, et al., Clinical Science, 94, pp. 239–243, 1998.

Nontraditional Coronary Risk Factors and Vascular Biology: The Frontiers of Preventive Cardiology, by P. Ridker et al., J. of Investigative Medicine, vol. 46, No. 8, Oct., 1998, pp. 348–350.

(List continued on next page.)

*Primary Examiner*—Cary O'Connor
*Assistant Examiner*—Catherine McPherson
*Attorney, Agent, or Firm*—Robert C. Kain, Jr.

[57] ABSTRACT

The calibrated method for characterizing blood flow in a limb of a patient during reactive hyperemia utilizes a blood pressure cuff. The method establishes a predetermined, near diastolic, pressure in said blood pressure cuff during the reactive hyperemic episode, continually senses the pressure in the cuff and periodically changes the internal volume of said blood pressure cuff by a predetermined volumetric amount to calibrate the system. The resultant change in the pressure is a calibration pressure pulse and is used to calculates pulsatile blood volume through the blood vessel. A calibrated method for determining the condition of blood vessels and endothelium includes determining, for each calibration cycle, a respective peak value for the blood volume and comparing the peak blood volume values with peak blood volume values for healthy blood vessels and endothelium. The comparison preferably utilizes a waveform. The calibrated system for characterizing blood flow includes a computerized electronic and pneumatic system which inflates, for a predetermined pre-test time, the blood pressure cuff to a suprasystolic pressure and thereafter establishes the near diastolic pressure in the cuff during the ensuing reactive hyperemic episode. A sensor substantially continually senses the pressure and generates a pressure signal. A subsystem periodically changes the volume of said blood pressure cuff during a calibration cycle. A corrected and calibrated blood volume signal is calculated with the calibration pressure signal. A calibrated system for determining the condition of blood vessels and endothelium is also disclosed.

59 Claims, 9 Drawing Sheets

OTHER PUBLICATIONS

Clinical Implications of Endothelial Dysfunction, C. Pepine, Clinical Cardiology, vol. 21, Nov., 1998, pp. 795–799.

Research Interests: nitric oxide; cyclic GMP; cell signaling; second messengers; regulatory biology, molecular pharmacology, F. Murad, Nov. 15, 1998, http://girch z.med.uth.tmc.edu/faculty/fmurad/index.cfm.

Nitric Oxide and Cyclic GMP Signal Transduction Mechanisms, L. Ignarro, Nov. 15, 1998, http://www.nuc.ucla.edu/html—docs/faculty—docs/ignarro.html.

The Nature of Endothelium–Derived Relaxation Factor, R. Furchgott, Nov. 16, 1998, http://www.hscbklyn.edu/pharmacology/furch.htm.

Impaired Vasodilator of Forearm Resistance Vessels in Hypercholesterolemic Humans, M. Creeger et al., J. Clinical Investigation, Jul., 1990, vol. 86, pp. 228–234.

Cigarette Smoking is Associated with Dose–Related and Potentially Reversible Impairment of Endothelium–Dependent Dilation in Healthy Young Adults, D. Celermajer et al., Nov., 1993, Circulation, vol. 88, No. 5, pp. 2149–2155.

Flow Dependent Coronary Artery Dilatation in Humans, H. Drexler, et al., Sep., 1989, Circulation, vol. 80, No. 3, pp. 466–474.

Non–invasive detection of endothelial dysfunction in children and adults at risk of atherosclerosis, D. Celermajer et al., Nov., 1992, The Lancet, vol. 340, No. 8828, pp. 1111–1115.

Abnormal Endothelium–Dependent Vascular Relaxation in Patients with Essential Hypertension, J. Panza et al., New England Journal of Medicine, Jul. 5, 1990, vol. 323, No. 1, pp. 22–27.

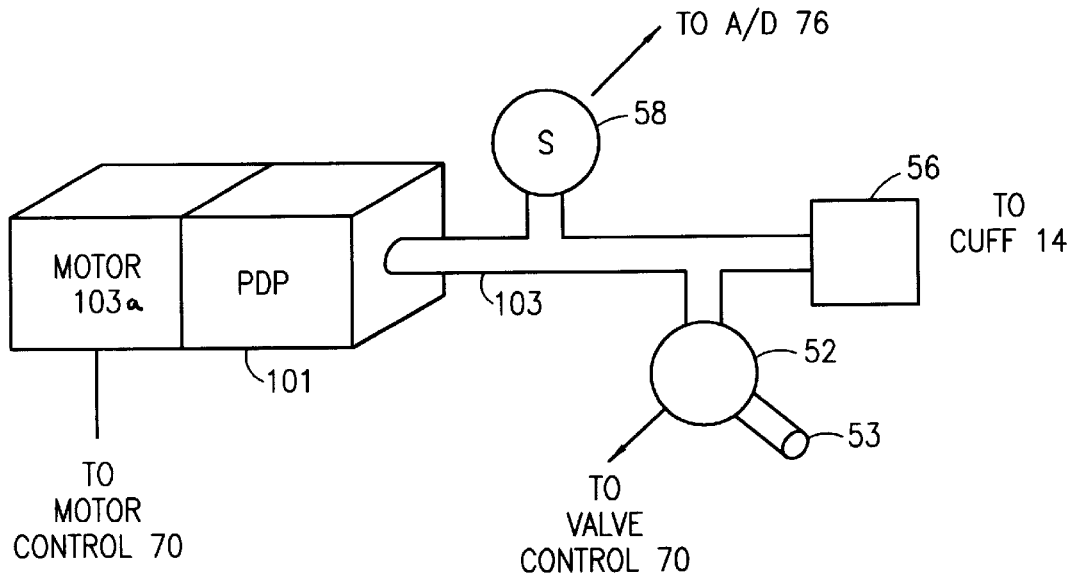
FIG. 4
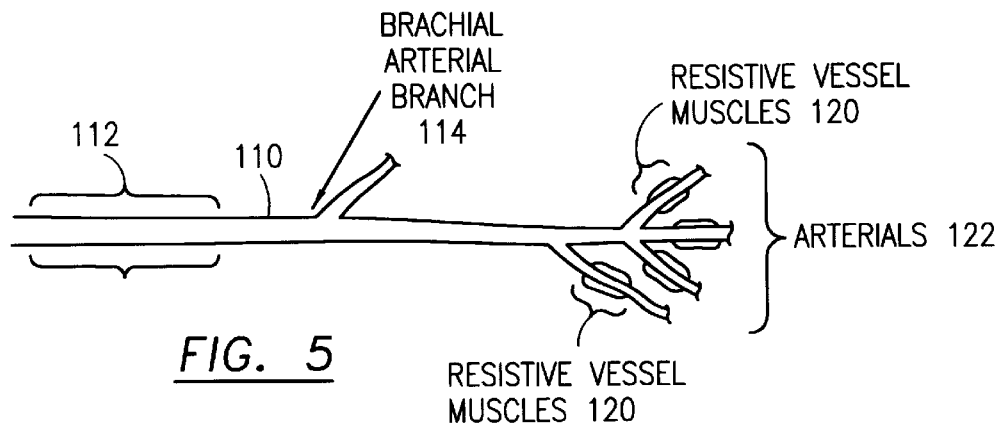
FIG. 5
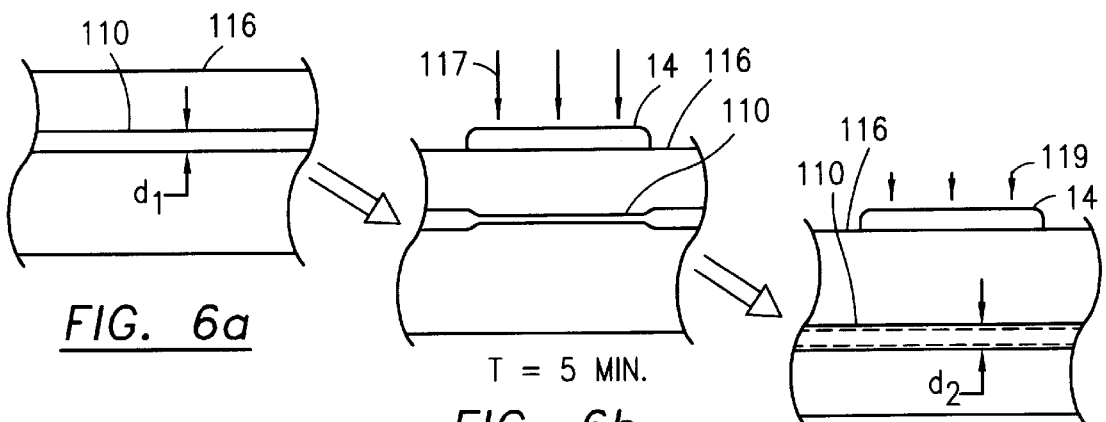
FIG. 6a
FIG. 6b
FIG. 6c

CALIBRATED MEASUREMENT OF BLOOD VESSELS AND ENDOTHELIUM AFTER REACTIVE HYPEREMIA AND METHOD THEREFOR

The present invention relates to the calibrated measurement of blood vessels, particularly arterial blood vessels, and the physiologic change of the endothelium, resulting from the generation of nitric oxide (NO), after reactive hyperemia and a method therefor.

BACKGROUND OF THE INVENTION

Researchers have observed that endothelial dysfunction is an early event in the pathogenesis of cardiovascular disease. The role of endothelium in maintaining cardiovascular health is fairly well documented. Endothelial dysfunction and coronary artery disease (CAD) are also linked to hypertension, hypercholesterolemia diabetes mellitus and cigarette smoking. Dietary and lifestyle modification, in addition to anti-oxidant vitamin supplementation, have been demonstrated to have a beneficial affect on endothelial function. Clinical Implications of Endothelial Dysfunction, C. Pepine, Clinical Cardiology, Vol. 21, November, 1998, pp. 795–799. Other researchers have observed that the vascular endothelium, the cells lining the interior portion of arteries, plays a fundamental role in several processes related to hemostasis thrombosis. These researchers have proposed that endothelial function may provide guidance to developing new strategies for coronary disease prevention and treatment. Nontraditional Coronary Risk Factors and Vascular Biology: The Frontiers of Preventive Cardiology, by P. Ridker et al., J. of Investigative Medicine, Vol. 46, No. 8, October, 1998, pp. 348–350. At present, the full range of different diseases associated with endothelial dysfunction remains to be determined, the nature of the abnormalities defined and measured, and the effects of potential treatments evaluated.

To some degree, the health and the condition of the endothelium is also related to the ability of that cellular layer to generate and transmit nitric oxide (NO) as a biomarker throughout the tissues of the arterial wall. Most recently, Nobel Prize winners Robert F. Furchgott, Ferid Murad and Louis J. Ignarro have linked the production and transmission of NO through the endothelium as being the primary indicator associated with vascular dilation. Previously, researchers theorized that vascular dilation was triggered by an agent named "endothelium-derived relaxing factor" or EDRF. With the association established by Furchgott, Murad and Ignarro, researchers now believe that NO is the dominant, if not exclusive EDRF and is directly related to the health and condition of the endothelium and the ability of the endothelium to dilate the arteries of a person. The Nature of Endothelium-Derived Relaxation Factor, R. Furchgott, Nov. 16, 1998, at the "www" website hscbklyn.edu/pharmacology/furch.htm; Research Interests: nitric oxide; cyclic gmp, cell signaling, second messengers, regulatory biology, molecular pharmacology, F. Murad, Nov. 15, 1998, at the "http" website girch z.med.uth.tmc.edu/faculty/fmurad/index.cfm; and, Nitric Oxide and Cyclic GMP Signal Transduction Mechanisms, L. Ignarro, Nov. 15, 1998, at the "www" website nuc.ucla.edu/html-docs/faculty-docs/ignarro.html. Accordingly, current research now indicates that NO is generated by the endothelium and is transmitted through the endothelium and that NO is a biomarker for vascular dilation.

Medical professionals have, in the past, sought to determine the health of a patient's vascular system by monitoring the physiological conditions or characteristics of the arteries in a patient's limb after reactive hyperemia. Reactive hyperemia occurs in a patient after a major artery has been blocked off or closed by a blood pressure cuff inflated slightly above systolic pressure for approximately five minutes. The limb, downstream from the blocked artery, suffers anoxia or severe hypoxia. Upon a sudden release of the blood pressure cuff, the endothelial cells lining the interior of the arterial wall react by generating NO and by dilating. This vascular dilation and expansion results in the expansion of resistive arterial vessels and associated muscles significantly downstream from site of the previously collapsed artery. The resistive arterial vessels enlarge based upon the NO biomarker, transmit NO through other parts of the endothelium and may cause reactive hyperemia in the limb. Reactive hyperemia is a significantly greater flow of blood through an artery, vein or limb as compared with normal blood flow therethrough. Blood flow is a characteristic of the artery and is typically a quantitative measurement of blood volume with respect to time (e.g. ml per minute). Generally, the phenomenon of reactive hyperemia lasts up to 10 minutes before return to pre-test pulse volume values.

Some medical professionals utilize pulse volume recorders to measure the peak pressure (mmHg) in the arteries immediately after the release of the blood pressure cuff and ischemia. However, these researches measure only the peak pressure during the reactive hyperemia and typically do not continuously measure blood volume or blood flow or the pulsatile blood volume change through the arteries in the limb during the entire reactive hyperemia episode, i.e., until return to the pre-episode state. The methods of pulse volume measurements have not been standardized by a national consensus panel of investigators.

Other researchers studying the effect of reactive hyperemia on a vascular system utilize ultrasound imaging techniques to capture an image of the brachial artery (the artery which is blocked to achieve reactive hyperemia in the arm of the patient) and measure the changing diameter of the brachial artery. Technicians measure the diameter of the artery before the ischemia (prior to reactive hyperemia and closure of the vascular system) by capturing electronic ultrasonic images. Subsequently, technicians attempt to detect and measure the largest expansion of the diameter of the brachial artery after ischemia and during the reactive hyperemia episode. These medical professionals then compute (with simple geometric equations) the expansion of the artery and the volume change of the artery. However, the use of an ultrasound image to measure the expansion of the brachial artery during reactive hyperemia has many technical problems that may jeopardize the measurement's accuracy and precision.

Researchers have observed that the brachial artery diameter typically expands about 0.3 mm during reactive hyperemia. Reproducibility of Brachial Ultrasonography and Flow-Mediated Dilation (FMD) for Assessing Endothelial Function, by K. L. Hardie, et al., Australian New Zealand Journal of Medicine, 27, pp.649–652, 1997 (this study revealed arterial diameter of 3.78 mm at rest; 3.89 mm during reactive hyperemia). Other studies show diameters of 3.92 mm at rest increasing to 4.13 mm during reactive hyperemia. Noninvasive Assessment of Endothelium-Dependent Flow-Mediated Dilation of the Brachial Artery, by A. Uehata et al, Vascular Medicine 2, pp. 87–92, 1997. Studies have shown that the effect of nitroglycerin treatment during reactive hyperemia increases the expansion of the arterial diameter by about 11%. Flow-Induced Vasodilation of the Human Brachial Artery is Impaired in Patient [over]

40 years of Age with Coronary Artery Disease, by E. Lieberman, et al., American Journal of Cardiology, 78, pp. 1210–1214, 1996. Nitroglycerin is converted into NO and this additional NO stimulates vascular dilation. This study has indicated that young people, without any indication of coronary artery disease (healthy individuals), exhibit an increase in the diameter of the brachial arterial on the order of 6.2%. In contrast, young people with coronary artery disease exhibit an arterial diameter increase of only 1.3%. This same study measured arterial diameters utilizing ultrasonic techniques and revealed measurement errors of plus or minus 1.1% for the diseased population typical (arterial expansion of 1.3%). Errors of 0.7% were noted during the ultrasonic measurement of the brachial arteries in the healthy population (typical arterial change of 6.2%). Accordingly, these studies show a coefficient of error or variation of almost 30% with utilization of ultrasonic techniques. These errors are caused by the acquisition of the electronic image data capturing the expansion of the brachial artery during reactive hyperemia, the measurement of the electronic image and the introduction of arithmetic errors into the calculation of the arterial diameter.

Currently, many researchers utilize ultrasonic techniques to noninvasively detect the increase of the diameter of the artery during reactive hyperemia. The use of ultrasonic imaging techniques has many problems. For example, the ultrasound technician operator must carefully place the ultrasound scanning head on and above the brachial artery at a certain x-y and z position relative to the patient's skin. The ultrasound head is typically placed a few inches above the crease in the patient's elbow. If the operator places the ultrasound head at a different location on another patient or if the operator places the ultrasound head at a different location on the same patient at a different clinical testing time, the data obtained during these inter-patient and intra-patient tests is not consistent. Further, the ultrasound operator must place the ultrasound head on the patient, move the ultrasound head longitudinally up and down the patient's arm, move the head laterally side to side about the arm and rotate the angle of the ultrasound head relative to the surface of the skin in order to obtain a clear electronic image of the brachial artery. This involves multiple eye-hand coordination by the operator since the operator views the image while he or she moves the ultrasound head over the patient's arm. Further, after the operator correctly positions and obtains a clear electronic image, the operator must then issue (a) a cuff release command to begin the reactive hyperemia and (b) a record command to the ultrasound equipment which begins recording the image. The ultrasound operator may also be required to move electronic calipers on the captured electronic image at the same time as he or she is capturing additional images in order to measure the expanded diameter of the brachial artery during reactive hyperemia. Specifically, the ultrasound operator quickly releases the blood pressure cuff which occluded the brachial artery for about five (5) minutes and initiates reactive hyperemia in the limb. During the first minute after cuff release, the ultrasound operator carefully positions the ultrasound head on the skin of the patient. During the next thirty seconds, the operator captures the ultrasound image of the expanded diameter of the brachial artery as a recorded electronic image and measures the increase of the arterial diameter. This measurement normally includes the use of electronic calipers on the display screen. In the third sixty second period, the operator continues to electronically monitor and store the image of the brachial artery as the arterial diameter reduces in size during the latter portions of the reactive hyperemia episode.

After the ultrasound operator captures this electronic image, the operator or other health professional can view or re-play the stored electronic image and seek to identify the largest expansion of the diameter of the brachial artery. Accordingly, it is difficult to obtain this data with ultrasound equipment, to replicate the test on the same patient, to replicate the same test on a different patient, to interpret the electronic image and to quantify the amount of arterial expansion.

These problems with respect to ultrasound imagery and the interpretation of the captured image have inhibited researchers from reproducing earlier experiments and confirming experiments conducted by other researchers and combining or correlating data from various studies. The current lack of standardization of methods prevents definitive studies among investigators.

Further, since ultrasonic imagery measures only an increase in the diameter of an artery, any error introduced by this measurement is amplified since it is squared in the mathematic formulas for the area A of a circle and the volume V of a tubular structure such as an artery. The equation for area A follows:

$$A = (\tfrac{1}{4})\pi d^2 \qquad \text{Eq. 1}$$

The equation for the volume V of a cylinder follows.

$$V = (\tfrac{1}{4})\pi d^2 l \qquad \text{Eq. 2}$$

The length of the ultrasound head is utilized to estimate the length l of the generally cylindrical arterial vessel. This formula establishes the volume of the arterial segment and the change in volume of the arterial segment during reactive hyperemia. Accordingly, any error introduced into the measurement of the diameter d of the artery is squared by the volumetric formula Eq. 2 and the system operator can only estimate the length l of arterial segment based upon the size of the ultrasound head. This estimate of length l also introduces another element of error into the measurement of the volumetric change of the blood vessel during reactive hyperemia.

U.S. Pat. No. 5,718,232 to Raines, et al. and U.S. Pat. No. 5,630,424 to Raines, et al. describe a calibration system for measuring segmental blood volume changes in arteries and veins for pulse volume recorders. The pulse volume recorders described in Raines '232 and Raines '424 add or subtract a predetermined volume (approximately 1 ml) to or from the volume of the pneumatic blood pressure cuff system at each cuff pressure over a plurality or multiple levels of induced cuff pressure. Basically, Raines '232 and Raines '424 seek a solution to the problem that the pneumatic response of the blood pressure cuff system due to blood pressure pulse waves changes at each discrete level of induced cuff pressure (the response delta P changes at each cuff lever Pcuff 40, 50, 60, 70, 80, and 90 mmHg.). In order to measure and calibrate the blood pressure system at each discrete cuff level, the predetermined volumetric amount is added or withdrawn from the pneumatic system at that induced cuff pressure level. By measuring the pressure change at the time of the volumetric calibration pulse, the resulting pressure wave signal is a calibration pressure pulse. The sensed pressure wave signal at the induced cuff pressure is converted into a corrected blood volume signal using the ratio of the volumetric calibration pulse versus the calibration pressure pulse. This is a direct measurement of blood volume and a basis for blood flow at the induced pressure level.

Specifically, the Raines '232 and the Raines '424 patents utilize a blood pressure cuff placed around the limb of a patient. The blood pressure cuff was pumped up or inflated to certain predetermined cuff levels such as 40, 50, 60, 70 mmHg through 120 mmHg. At each discrete cuff pressure level Pcuff, the system was calibrated in order to obtain a corrected blood volume signal change at each cuff pressure level. After the corrected blood volume data was obtained, a ratio was generated between blood volume change in relation to the pressure change at the selected induced cuff pressure in order to determine the maximum value of the blood volume versus the sensed pressure differential. The maximal ratio of blood volume change versus blood pressure change at a particular cuff pressure provides an indication of the onset and the degree of atherosclerosis in humans as well as provides an indication of the health or condition of the vascular system and particularly of the peripheral vascular system. The contents and substance of U.S. Pat. No. 5,718,232 to Raines et al. and U.S. Pat. No. 5,630,424 to Raines et al. is incorporated herein by reference thereto. The relationship between atherosclerosis and the maximal ratio of delta V over delta P (peak arterial compliance) is disclosed in U.S. Pat. No. 5,241,963 to Shankar. The content of U.S. Pat. No. 5,241,963 is incorporated herein by reference thereto.

OBJECTS OF THE INVENTION

It is an object of the present invention to provide acalibrated measurement system to measure the dilation of blood vessels in a patient's limb and to measure the endothelium after reactive hyperemia.

It is an additional object of the present invention to provide a calibrated measurement system to measure the dilation of arterial blood vessels and to indirectly measure the endothelium's production of NO and the arterial dilation response to the NO after reactive hyperemia. Also, it is an object of the present invention to measure those items before and after the administration of other agents producing similar alterations of arterial reactions.

It is another object of the present invention to provide a method for obtaining a calibrated measurement of blood vessels and endothelium after reactive hyperemia.

It is an object of the present invention to provide a clinical diagnostic and evaluation method for obtaining a calibrated measurement of the change of volume of arterial blood vessels and endothelium after production of reactive hyperemia.

It is a further object of the present invention to provide an internal calibration system for measuring the dilation of blood vessels and the effects on the endothelium during the entire reactive hyperemia episode.

It is additional object of the present invention to capture pressure pulse data (which may be waveform and/or tabular data), periodically calibrate the pneumatic system, and calculate the blood volume data and waveform, if necessary, and the blood flow (q versus t) during the entire reactive hyperemia episode. The data capture and processing is preferably, essentially continuous, however, the processing may be conducted during a post-examination time or off-line rather than in real time, during the reactive hyperemia (RHT) test.

It is another object of the present invention to provide multiple and periodic calibrations of the pneumatic system during the entire reactive hyperemia episode.

It is an additional object of the present invention to provide a pneumatic system which automatically initiates the quick pressure release of the blood pressure cuff pneumatic system, quickly achieves a predetermined diastolic or near diastolic cuff pressure in the blood pressure cuff pneumatic system and monitors and calibrates pressure pulse waves during substantially all of the reactive hyperemia episode.

It is an additional object of the present invention to measure the effects of reactive hyperemia on all the blood vessels (primarily arterial blood vessels) and endothelium of the patient rather than simply the brachial artery of the patient. Further, the RHT test may be conducted on the major distal portion of each of the four limbs of the patent. This technique potentially enhances the quality of test's overall results.

It is a further object of the present invention to plot, map and/or record calibrated blood volume data and/or the blood flow data during substantially all of the reactive hyperemia episode in order to correlate the health and condition of the endothelium and the coronary artery system based upon the effects of the reactive hyperemia on the limb of patient.

It is another object of the present invention to compare normal blood volume data and normal waveforms showing the pulsatile component of blood flow during substantially all of the reactive hyperemia episode with other data and waveforms from patients exhibiting healthy blood flow and cardiovascular disease and coronary artery disease in order to provide a noninvasive method and noninvasive system to measure coronary artery disease based upon the response and condition of the endothelium during reactive hyperemia.

It is another object of the present invention to automatically perform a reactive hyperemia test on a plurality of patients and/or a number of reactive hyperemia tests on a single patient with a high degree of accuracy, precision and repeatability in order to reduce interpatient and intrapatient errors. This objective greatly enhances the creation of definitive studies among investigators.

It is a further object of the present invention to provide measurements of pulse waveform and blood volume and to automatically gather that data with a minimum of error and bias. As explained herein, prior art techniques utilizing ultrasound machines and imaging techniques involve a considerable degree of operator intervention and hence, result in an unacceptable amount of operator error in the reported results.

It is another object of the present invention to provide frequent and continuous measurement of the pulse volume response which enables detection of inter-test and/or inter-patient differences, the magnitude of the responses that may be associated with the time-based phases of hyperemic response, i.e., the maximum response occurring in the early, mid-range, late or prolonged response.

SUMMARY OF THE INVENTION

The calibrated method for characterizing blood flow in a limb of a patient during reactive hyperemia utilizes a blood pressure cuff. The method establishes a predetermined, diastolic or near diastolic pressure in the blood pressure cuff during the reactive hyperemic episode, continually senses the pressure in said blood pressure cuff during the reactive hyperemic episode, and periodically changes the internal volume of said blood pressure cuff by a predetermined volumetric amount. This volumetric change establishes a calibration cycle. The method concurrently senses a resultant change in the pressure as a calibration pressure pulse and calculates pulsatile blood volume through the blood vessel by correcting the sensed pressure with the ratio of the predetermined volumetric amount and calibration pressure pulse. A calibrated method for determining the condition of blood vessels and endothelium includes determining, for each calibration cycle, a respective peak value for the blood volume, and comparing the peak blood volume values for the plurality of calibration cycles encompassing the reactive hyperemia episode with peak blood volume values for healthy blood vessels and endothelium during reactive hyperemia. The comparison is preferably made with acquired blood volume data or waveform and stored data or waveform showing peak blood volume values for healthy blood vessels and the characterization of the endothelium during reactive hyperemia.

The calibrated system for characterizing blood flow includes a computerized electronic and pneumatic system which inflates, for a predetermined pre-test time, the blood pressure cuff to a suprasystolic pressure and thereafter establishes the diastolic or near diastolic pressure in the cuff during the ensuing reactive hyperemic episode. A sensor substantially continually senses the pressure in the cuff and generates a pressure signal, particularly a pressure pulse signal. A subsystem periodically changes the volume of the blood pressure cuff by a predetermined volumetric amount in a calibration cycle. A calibration pressure pulse signal is generated based upon a resultant change in the pressure signal. A blood volume signal is generated by correcting the sensed pressure signal with a ratio of the predetermined volumetric amount and the calibration pressure pulse signal. A calibrated system for determining the condition of blood vessels and endothelium includes the aforementioned elements and a computerized system for determining, for each calibration cycle, a respective peak blood volume value and for comparing the acquired peak blood volume values with a plurality of predetermined peak blood volume values representing healthy blood vessels and endothelium during reactive hyperemia. Typically, these are graphically presented and displayed as waveforms. Alternatively, data table presentations are provided to the operator.

BRIEF DESCRIPTION OF THE DRAWINGS

Further objects and advantages of the present invention can be found in the detailed description of the preferred embodiments when taken in conjunction with accompanying drawings in which:

FIG. 4 diagrammatically illustrates another embodiment of the pneumatic system to obtain the calibrated measurements described herein and the pressure pulse waveforms in accordance with the principles of the present invention;

FIG. 5 diagrammatically illustrates an arterial system which is monitored to measure the health of the endothelium, the transmission of nitric oxide NO and which provides an indicator of the health and condition of the patient's cardiovascular system;

FIGS. 6a, 6b and 6c diagrammatically illustrate the method of achieving reactive hyperemia and dilation of the brachial artery;

DETAILED DESCRIPTION OF THE PREFERRED EMBODIMENTS

The present invention relates to a calibrated measurement of blood vessels and endothelium after reactive hyperemia and a method therefor. Particularly, volume and flow through the arterial blood vessels is measured by the method and the apparatus.

Figure 1:
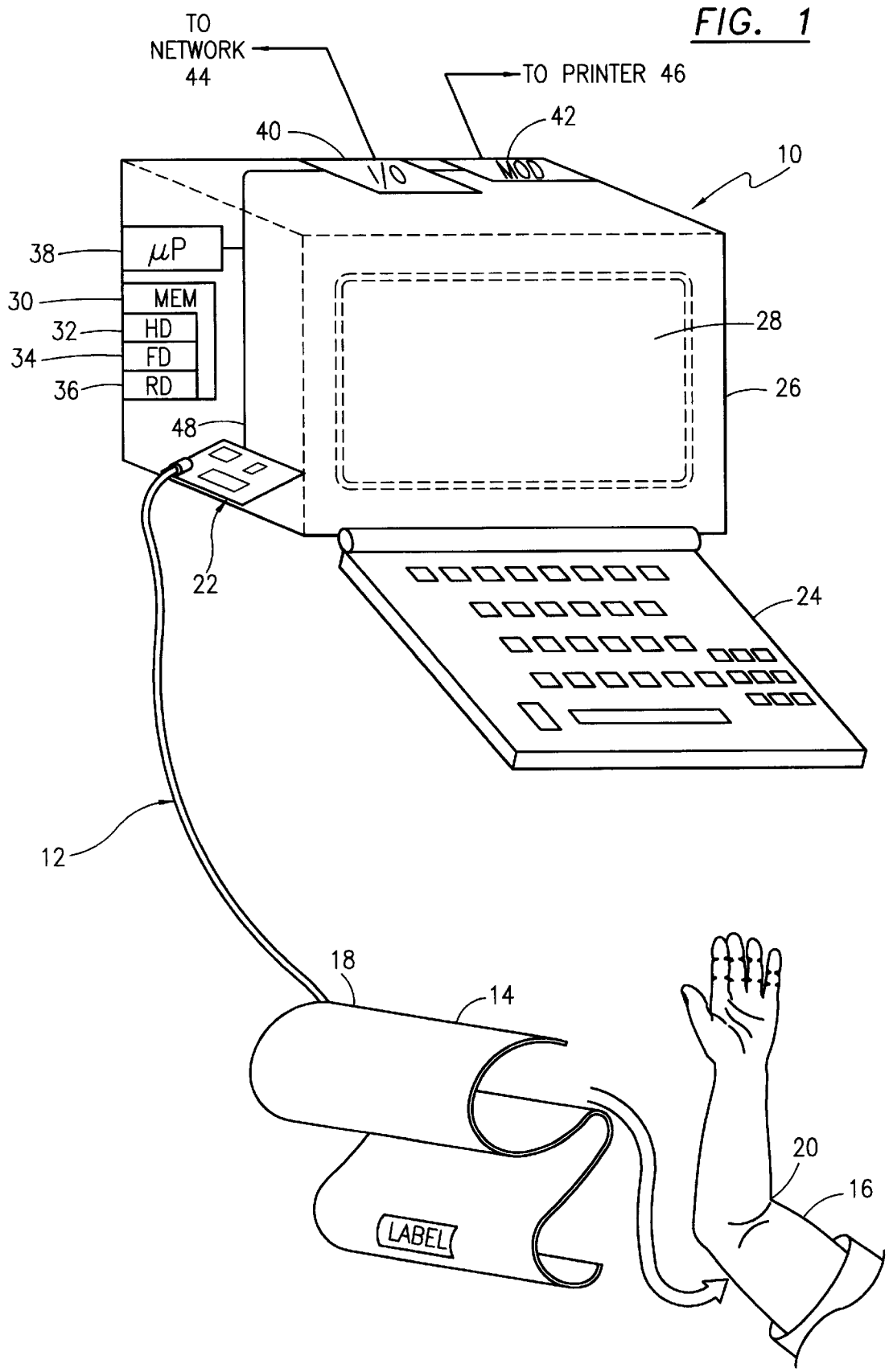
FIG. 1 diagrammatically illustrates a computer system and the major functional components of an electronic and a pneumatic system for the calibrated measurement of blood vessels and endothelium after reactive hyperemia and method therefor in accordance with the principles of the present invention.

FIG. 1 diagrammatically illustrates the basic components of a computer or an electronic system 10 and a pneumatic system 12 used in connection with the calibrated measurement of blood vessels and the endothelium after reactive hyperemia. Due to the continual reduction in price, improvement in quality and integration of electronic and computer components, FIG. 1 diagrammatically illustrates functional elements of the invention. Accordingly, the claims appended hereto are meant to cover the future integration of electronic components. Pneumatic system 12 includes a blood pressure cuff 14 that is adapted to be wrapped around the upper arm 16 of a patient. Particularly, since it is important to correctly locate cuff 14 on upper arm 16, cuff 14 may include a label with written instructions instructing the operator to place cuff edge 18 a certain distance from elbow crease 20 of the patient's limb. The objective is to locate the cuff, on a regular basis, at a standard, specified and constant location or distance above the antecubital crease or fold. The pneumatic system described herein preferably utilizes a blood pressure cuff which is designated as the "standard" or predetermined cuff used for all the machines and used in connection with all methods described herein. The use of "standard" or a single type of cuff results in the establishment of a constant sized occlusion or blockage of the arteries in the limb of the patient. The relative dimensional sizes of the components in FIG. 1 are not accurate. As explained in detail later, cuff 14 is wrapped around upper arm 16, inflated for a 5 minute period to collapse the arteries and veins in limb segment 16, thereby achieving ischemia in the limb and the downstream portions of the limb. Blood pressure cuff 14 is inflated, deflated and controlled based upon pneumatic and electronic components on system board 22. System board 22 is explained in detail later in connection with FIGS. 2–4.

The computer system 10 includes a keyboard or keypad 24 (and may further include a mouse, trackball or other pointing device, not shown), a main CPU box 26, a display screen or monitor 28, and a memory system 30. Memory system 30 includes hard drive 32, floppy drive 34, removable drive 36 and possibly a ZIP drive or comparable removable tape drive (not shown). A CDROM writer may also be used to write data to a CDROM. The computerized system 10 also includes a microprocessor 38, an input/output unit 40 and, in a preferred embodiment, a modem 42. The modem enables connection to the Internet. Input/output unit 40 may be connected to a computer network 44 (local area network or wide area network) and/or a printer 46.

Microprocessor 38 utilizes computer programs stored in memory 30, which includes hard drive 32, floppy drive 34 and removable drive 36, as necessary, as well as random access memory RAM and readonly memory ROM (included in memory 30). The microprocessor obtains, processes and stores data with the assistance of the memory 30 and under the control of programs stored in memory 30. Microprocessor 38 controls various peripheral equipment via input/output unit 40. These peripherals include display 28, modem 42, printer 46 and network card or board 44. The input/output unit 40 also controls keyboard 24 and any associated mouse or other operator input control. Microprocessor 38 is connected to these various electronic components and to the system electronic/pneumatic unit 22 via a bus 48.

Figure 2:
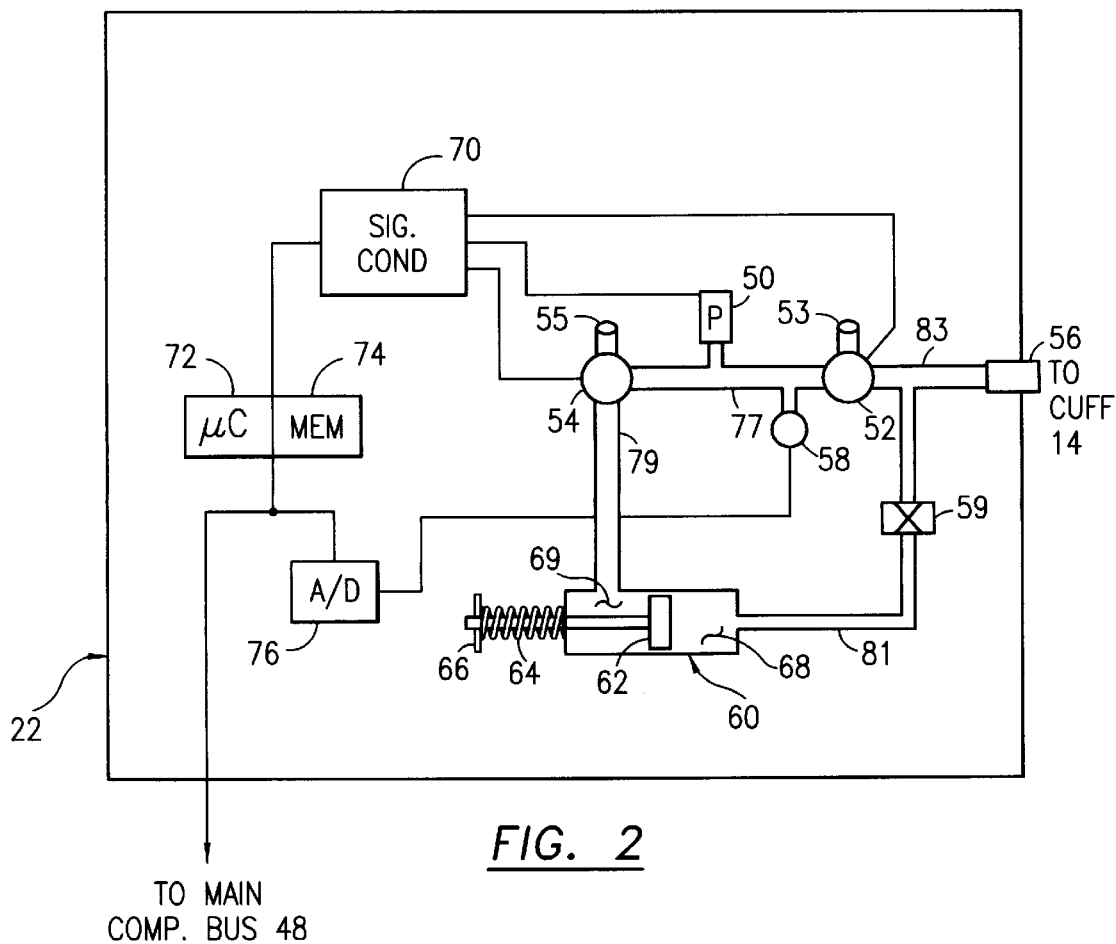
FIG. 2 diagrammatically illustrates an electronic and pneumatic system for generating cuff pressures, calibrating the cuff pressures and capturing pressure pulse wave data in accordance with the principles of the present invention.
Figure 3:
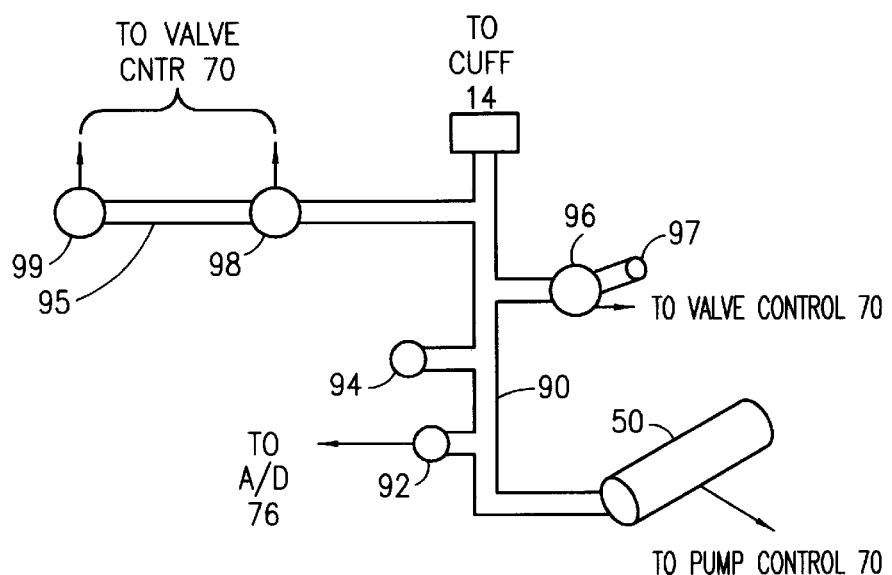
FIG. 3 diagrammatically illustrates an alternate pneumatic system to obtain calibrated signals and pulse pressure waveforms in accordance with the principles of the present invention.

FIGS. 2–4 diagrammatically illustrate various pneumatic and electronic systems to measure the dilation of blood vessels and actions of the endothelium with reactive hyperemia as well as to create the reactive hyperemia in the patient's limb. FIG. 2 diagrammatically illustrates the preferred embodiment. However, the systems in FIGS. 3–4 may be utilized to achieve substantially the same results.

In FIG. 2, a pump P 50 is pneumatically connected to valves 52 and 54 via line or tube 77. Main valve 52 is pneumatically connected via line 83 to blood pressure cuff coupling 56. Pressure sensor 58 is also pneumatically linked to line 77, pump 50 and valves 52, 54. Sensor 58 monitors the air or other pressure in the blood pressure cuff system. This pressure sensor substantially continually monitors pressure based upon a pre-programmed sampling rate. Although unlikely, a hydraulic system may be utilized rather than a pneumatic blood pressure cuff system. This hydraulic embodiment is unlikely because of the wide acceptance of pneumatic blood pressure cuff systems by the medical community.

Main valve 52 has a primary pneumatic output that is further pneumatically linked to a resistive pneumatic element 59. The positioning of main valve 52 may be changed such that resistive element 59 is at its input. Piston system 60 is pneumatically coupled at an intermediate position relative to resistive element 59 and secondary valve 54. Piston system 60 includes piston head 62 which is biased forward by spring 64 mechanically acting on stop 66. The face of piston 62 effects the volume of chamber 68 in piston system 60. The backside of piston head 62 is effected and acted on by the air pressure in the backside chamber 69. This air pressure in backside piston chamber 69 is controlled by secondary valve 54 which is pneumatically linked to the backside of the chamber.

Main valve 52 and secondary valve 54 both include exhaust ports 53, 55. Ports 53, 55 may be quick action valves.

Pump 50, main valve 52 and secondary valve 54 are controlled by electronic signals supplied by and supplied through signal conditioner 70. Signal conditioner 70 is an interface between the valves and the balance of the electronic system. The signal conditioner 70 may be incorporated into the other electronic devices or may include several discrete electrical components. The pump drive signals and valve control signals are generated by a microcontroller 72 in accordance with programs stored in memory 74. Memory 74 may include random access memory, read only memory or may be incorporated into computer system memory 30. Further, microprocessor 72 and memory 74 may be replaced with programmable logic or erasable programmable read only memory (EPROM) or programmable read only memory (PROM) as appropriate. In the preferred embodiment, the electronic and pneumatic system board 22 includes an on-board microprocessor and an on-board memory in order to generate pump control and valve control signals via signal conditioner 70 to main valve 52, pump 50 and secondary valve 54.

Pressure sensor 58 is electronically monitored by analog to digital A/D converter 76. The output of A/D converter 76 is connected to microprocessor 72 and memory 74 and also to the main computer bus 48. It should be noted that microprocessor 72 and memory 74 may be replaced by and integrated with main microprocessor 38 and memory 30 in computer system 10. This integration may depend upon the speed of microprocessor 38 and multi-tasking capability of that microprocessor as well as the cost of an on-board microprocessor 72. Pressure data signals may be temporarily stored in on-board memory 74 dependent upon the architecture of the electrical hardware and software.

In operation, the electronic and pneumatic system illustrated in FIG. 2 operates in the following manner. Main valve 52 closes. Secondary valve 54 is opened and exhausts any pressure in pneumatic lines 77 and 79 by venting the subsystem to the ambient pressure environment via exhaust port 55. Secondary valve 54 then closes and pump 50 is activated. Main valve 52 is opened. Pump 50 is commanded to inflate cuff 14 (FIG. 1) to a suprasystolic pressure level which effectively collapses or occludes all the arteries in the upper arm 16 of the patient. A suprasystolic pressure is a pressure greater than the patient's highest level of blood pressure in his or her vascular system. In one working embodiment, the supra-systolic pressure is 20 mmHg above the previously obtained systolic pressure of the patient. The pressure in the pneumatic system (pneumatic line 77 and cuff 14) is substantially continually monitored by sensor 58, A/D converter 76 and ultimately microprocessor 72. A duplicate monitoring of the pressure signal may be implemented with main processor 38. In the event of a failure (mechanical, pneumatic or patient voluntary or involuntary interruption), microprocessor 72 stops pump 50 and opens main valve 52 and/or secondary valve 54 thereby venting pressure from the pneumatic system (line 77 and cuff 14) via exhaust port 55 and/or 53.

During normal operation, pump 50 is activated to pump up and pneumatically inflate cuff 14 until all the arteries in limb 16 collapse thereby blocking any blood flow through those arteries into the downstream portion of limb 16.

This condition is maintained for 5 minutes to achieve ischemia or extreme hypoxia in the patient's limb. This is a predetermined pre-test time period which is a standard used by most clinical investigators. This time may be shortened or lengthened based upon further experimentation. Pump 50 is turned OFF when pressure sensor 58 (and associated electronics) detects a predetermined suprasystolic pressure level in the pneumatic blood pressure cuff system (line 77, 83 and blood pressure cuff 14). The suprasystolic pressure level is generally specified at a level 20 mmHg above the subject's systolic pressure but other elevations may be used.

When the pneumatic blood pressure cuff system reaches the suprasystolic pressure (established either by (a) a predetermined value programmed into microprocessor 72 and memory 74 or programmed into main microprocessor 38 and memory 30 or (b) a predetermined level above the patient's systolic pressure), a timer or clock is initiated in the appropriate memory under the control of the appropriate microprocessor. Currently, the timers are maintained by main microprocessor 38 and memory 30. Upon the expiration of the predetermined time period (5 minutes), microprocessor 72 and memory 74 (under the ultimate control of main microprocessor 38 but the specific control of processor 72) commands main valve 72 to open its exhaust port 53 to quickly release pressure from the pneumatic system established by blood pressure cuff 14.

This quick release feature is one feature of the present system. An additional quick release exhaust valve may be added to the system if necessary (not illustrated). The further quick release system would be pneumatically coupled on line 83. The electronic output of pressure sensor 58 is monitored by microprocessor 72 until the pressure reaches the diastolic level or a near diastolic level. This quick release of cuff pressure is required in order to rapidly achieve reactive hyperemia in limb segment 16 and the downstream portions of that limb segment. As described in greater detail hereinafter, the calibrated system and the calibrated method in accordance with the principles of the present invention periodically calibrate the pneumatic system while acquiring pressure wave pulse data during reactive hyperemia.

The predetermined diastolic or near diastolic pressure level at which main valve 52 (or alternately valve 54) closes is determined in whole or in part upon the patient's diastolic or low blood pressure level. In one working embodiment, the predetermined pressure is 5 mmHg less that the measured diastolic pressure. Prior to initiating the test described herein, the medical professional obtains, via conventional methods or otherwise, the patient's diastolic (low level) and systolic (high level) blood pressures. A typical diastolic/systolic blood pressure (BP) is 120/60 mmHg. Normal systolic pressure in the range of 90–140 mmHg is reasonable. Diastolic pressure of 60 mmHg plus or minus 10 mmHg is reasonable. Since the diastolic pressure should be about 60 mmHg, the presently described system may be pre-set to close the exhaust valve during the quick release operational module at 60 mmHg. However another version, the system operator may be prompted to (a) obtain the patient's diastolic/systolic blood pressure/(BP); and (b) input that BP data into the system. In this event, the system may utilize the input diastolic pressure plus or minus a pre-set value (e.g. 5 mmHg) rather than the pre-set pressure of 60 mmHg. The term "near diastolic" is meant to cover these three variations.

In a further enhancement, the system may be configured to directly measure both BP data points prior to initiating reactive hyperemia in the patient. Electronic systems controlling and monitoring pneumatic systems to acquire and store diastolic and systolic blood pressure data are known in the biomedical industry. In a working embodiment, (a) the operator measures BP via conventional audio methods, (b) the operator inputs this data into the system, (c) the system inflates the cuff to 5 mmHg less then the measured diastolic pressure, (d) calibrates the data, (e) measures and computes $V_m$ and $Q_p$ (discussed later herein) and (f) then occludes the artery and initiates the hyperemia reactive test described in detail hereinafter.

Either of these pre-test procedures may be utilized to obtain, record and utilize a diastolic pressure level, or a pre-set value offset from diastolic pressure, as a predetermined base cuff pressure level. As explained later, the predetermined base pressure is easily convertible into a predetermined base blood volume level V and a predetermined base blood flow level Q. The term "level" as used herein is equivalent to the terms "data" or "value." The term "limb" or "arm" can refer to any of the body's limbs.

The system and method may also be modified to measure the physiologic condition of the blood vessels by monitoring blood pressure, pressure pulses, and hence blood volume, at a predetermined level above or below the patient's diastolic pressure (e.g. diastolic minus 5 mmHg.).

Returning to a brief description of the operation of the calibrated system and method, during each calibration cycle, secondary valve 54 is opened to vent pneumatic line 79 and exhaust the pressure from line 79 through exhaust port 55. Valve 54 may be able to independently vent line 79 separate from line 77. When the pressure is vented from pneumatic line 79, the pressure is reduced in back chamber 68 of piston unit 60.

At an earlier time, pneumatic line 79 and back chamber 69 held the same pressure as pneumatic line 77 and blood pressure cuff subsystem 14.

At the calibration trigger time, established by microprocessor 72 and memory 74 (optionally processor 38), secondary valve 54 vents pneumatic line 76 to the ambient environment via exhaust port 55. This also vents the pressure from back chamber 69. Piston head 62 then moves backwards against the biasing force of spring 64 a predetermined volumetric amount. Rearward movement of piston head 62 is caused by the pressure differential between chambers 68 and 69 (lines 81–83 and 79). This predetermined movement changes the internal volume in the pneumatic system (established by pneumatic lines 81, 83 and blood pressure cuff 14) by a predetermined volumetric amount. The biasing force of spring 64 and the movement of piston head 62 within chambers 68, 69 is carefully preset such that when piston head 62 moves and expands chamber 68, the expansion increases the volume of the pneumatic system (lines 81, 83 and pressure cuff 14) a predetermined volumetric amount. In a currently preferred embodiment, the volume change in the pneumatic system is 0.68 ml. Volume is added to the cuff system. In a different embodiment, volume may be subtracted from the cuff system by forcing piston head forward in chamber 68.

As explained in detail later, this volumetric calibration amount $V_{cal}$ is added at several times during the reactive hyperemia episode to the cuff system in order to recalibrate the system pursuant to realtime derived timing requirements. The timing requirements are keyed to the sensed pressure pulses. Frequent recalibration of the system is thought to be necessary for optimal accuracy and precision while repeatedly measuring small changes in the pressure pulse waveform. The pneumatic and electronic data acquisition system may drift thereby corrupting the data acquisition and processing. The system measures blood pressure pulse changes. More specifically, the system responds to blood pressure pulse volume changes in the arterial system in the patient's limb. Typically, the diameter of the brachial artery in an arm changes 1.3% to 6.2% during these blood pressure pulses.

Periodic recalibration avoids and eliminates the problems regarding pneumatic and electronic signal drift. Also, it has been established by preliminary testing that the response and the performance of the pneumatic system changes (a) during the hyperemia test (i.e., over time); (b) based upon the cuff pressure in the pneumatic system and (c) due to pneumatic and mechanical limitations in the current equipment. For example in one working embodiment, it is not possible to precisely and continuously maintain diastolic or near diastolic (5 mmHg below diastolic) pressure in the pneumatic system for 5–10 minutes hyperemic episode. This "leakage" or pneumatic drift may be due to many factors (e.g., the specific cuff used in the present experiments, the cuff's linkage to the pneumatic coupler on the PC board, the pneumatic system mounted on the PC board (unlikely, but possible), the type or quality of valves, pump or calibration cylinder used on the PC board). Some of these factors may be eliminated by improving the quality of the components or improving the interfit or mechanical interfaces between the components. However, it is unlikely that all pneumatic drift (presently on the order of about plus or minus 2–5 mmHg over five to ten minute hyperemic time frame) will be eliminated. Even if such drift is reduced by closer manufacturing tolerances and quality assurance programs, the projected high utilization rate of the machine (7–10 patients per day) and life cycle durability of the machine (grossly currently estimated at 3–5 years), it is inevitable that the "wear and tear" on the machine will cause pneumatic signal drift. Frequent and repeated calibrations during the RHT test significantly reduce, if not eliminate, this drift problem since pulse signals are captured based upon calibration triggers.

In U.S. Pat. No. 5,718,232 to Raines, et al., it is known that at each discrete induced cuff pressure level (50 mmHg, 60 mmHg, 70 mmHg . . . 120 mmHg), the pneumatic system provides a slightly different response to the blood flow through the patient's arteries (measured by blood pressure pulse data) than at other pressure cuff levels. The system response at 60 mmHg is different than the system response at 90 mmHg.

In the present invention, it is thought that since the response of the brachial arterial diameter during reactive hyperemia diminishes from 6.2% (a healthy arterial diameter response) to 1.3% (a diseased arterial diameter response), the periodic calibration of the pneumatic system measuring blood pressure pulse waves is necessary to obtain correct blood volume pulse wave data V during the entire 5–10 minute reactive hyperemia episode. The episode may last 10 minutes and the calibrated testing method described herein can be easily expanded to cover the longer 10 minute RHT test.

Further, the utilization of the internal calibration system described and claimed in connection with the present invention enables the medical community to gather blood volume pulse wave data and waveforms in a standardized, constant, reproducible and an automatic manner. By acquiring this blood volume pulse wave data utilizing standard calibration techniques, both repetitive calibration during the reactive hyperemia episode and the standardized nature of the calibration (withdrawing or injecting predetermined volumes from the pneumatic cuff system), further measurements of brachial artery dilation and performance and condition of the endothelium can be reproduced with different patient groups at many medical facilities by many researchers. The standardized collection of data will greatly advance the study of NO, endothelial reaction and blood vessel activity during reactive hyperemia.

One of the major drawbacks in the study of the health and condition or physiologic characterization of the endothelium and the effects of nitric oxide NO is the utilization of ultrasound data. Ultrasound techniques measure the diameter of the brachial artery during reactive hyperemia. As discussed in detail above, ultrasound data include operator errors, visual data acquisition errors and interpretation errors. The present data acquisition system is better for several reasons. Operator error is minimized because the instructions are on the cuff label and use of the method and the machine is simplified. Hand-eye coordination to acquire an image signal is eliminated. Operator placement of electronic calipers about an electronic ultrasound image to measure arterial diameter is eliminated. Lastly, blood volume change is directly measured without resort to visual measurements and compounding computational errors. Also, the present invention is absolutely non-invasive.

Since the present invention establishes an automatic and standardized calibration routine with volume additions or subtractions from the pneumatic system and periodic automatic calibration of the acquired signals during the entire reactive hyperemic episode, the study of the health, condition and physiologic characterization of the endothelium, the effects of NO, and the effects of drugs on NO and on the cardiovascular system can be easily standardized. Therefore, data can be shared among researchers to compare and contrast the effectiveness of drugs, the effects of lifestyle modifications, the cessation of smoking, and the effects of diet on the endothelium and the cardiovascular system. These are major objectives of the invention and a summary of the problems solved by the invention described herein.

FIGS. 3 and 4 diagrammatically illustrate other types of pneumatic systems. In FIG. 3, pump 50 is pneumatically connected to pneumatic line 90. Pressure sensor 92 is electronically connected to A/D converter 76 and is pneumatically connected to pneumatic line 90. Safety relief valve 94 insures that, if an adverse or other undesirable event occurs in the testing procedure, safety valve 94 opens and quickly vents the pressure in the pneumatic system to the ambient environment. Quick release valve 96 is utilized to quickly vent air from the pneumatic system which includes pneumatic line 90 and blood pressure cuff 14. The system is vented via exhaust 97. Valves 98 and 99 are utilized to add a predetermined volume into the pneumatic system. This predetermined volume is established by pneumatic chamber or line 95.

Briefly, when the pneumatic and electronic system is operating during the reactive hyperemia episode and the system is collecting blood pressure pulse wave data (see FIG. 10), the calibration steps include (a) opening valve 99 and exhausting the pressure in pneumatic line 95 while valve 98 is closed; (b) closing valve 99; (c) opening valve 98 at the calibration time thereby exposing the volume in chamber 95 (a calibrated volume $V_{cc}$) to the pneumatic system which includes pneumatic line 90 and blood pressure cuff 14; (d) detecting the pressure change $P_{CAL}$ with sensor 92; (e) computing the corrected blood volume pulse waveform based upon the ratio of the predetermined volume $V_{cc}$ added to the pneumatic system and the measured pressure calibration data $P_{CAL}$ and taking that ratio into account when computing the blood volume pulse waveform $V_n$ with the current diastolic pressure $P_d$ established as a base line. This computation of the blood volume pulse waveform is discussed in detail later.

FIG. 4 diagrammatically illustrates another embodiment of the pneumatic and electronic system. In this embodiment, pump motor control 70 is coupled motor 103a which is coupled to a positive displacement pump output 101 (the entire unit may be called a positive displacement pump) which is connected to pneumatic line 103. Pneumatic line 103 is connected pressure sensor 58 and main valve 52. Cuff coupler 56 is pneumatically and mechanically connected to blood pressure cuff 14. Main valve 52 has an exhaust port 53 and is electronically connected to valve control 70.

In operation, motor 103a drives positive displacement pump output 101 to initially pump up and achieve the correct air pressure in the pneumatic system which includes pneumatic line 103 and blood pressure cuff 14 (first supersystolic, then quick release, then diastolic pressure). In order to achieve calibration of the system, positive displacement pump output 101 is triggered to inject a predetermined volume $V_{cc}$ into the pneumatic system. The output of PDP pump 101, on line 103 is a predetermined volume of air. In a preferred embodiment, this injected volume is 1 ml. Sensor 58 then detects the change in the system pressure $P_{cal}$ and this calibrated pressure pulse $p_{cal}$ is utilized to compute the actual blood volume pulse waveform $V_n$ numerous times over a time period which includes the reactive hyperemia episode.

FIG. 5 diagrammatically illustrates some of the arterial system in limb 16 of the patient. FIG. 5 will be discussed concurrently with FIGS. 6a, 6b and 6c which diagrammatically illustrate the ischemia and subsequent dilation of the brachial artery during reactive hyperemia.

In FIG. 5, brachial artery 110 will be compressed and collapsed about region 112 by a compressive force placed about limb 16 (FIG. 1) of the patient with blood pressure cuff 14. Region 112 is upstream of the brachial arterial branch 114 (near the patient's elbow crease). In FIG. 6a, brachial artery 110 is diagrammatically illustrated beneath epidermis skin layer 116. At rest and in a sedentary position, brachial artery 110 of the patient has a diameter $d_1$.

In order to establish and record pressure pulse data and waveforms and calculate calibrated blood volume pulse data and waveforms, the patient should undergo certain pre-test preparations, be placed in a certain position and maintained in a certain condition during the test. In a preferred embodiment, the pre-test and test conditions will be specified in a defined and a standardized manner to establish a certain medical protocol. The following Pre-Study Patient Condition Table provides some examples, of a fundamental nature, of the condition of the patient prior to conducting the test to determine the state or condition of the endothelium with reactive hyperemia.

Pre-Study Patient Condition Table
patient sedentary and in a relaxed state
no food for more than 2 hours (possibly 12 hours) before test
no coffee or caffeine beverages for more than 1 hour before test
no smoking for more than 1 hour before test It has been established by other researchers that if a patient eats a high fat meal, e.g., a MC DONALD'S BIG MAC, within one hour prior to an ultrasonic test to measure brachial arterial diameter during reactive hyperemia, the patient's arteries, and hence the data, is adversely affected by the high amount of salt, dietary fat and cholesterol.

Other factors affect the condition of the endothelium and the generation NO by the endothelium and the dilation of the patient's cardiovascular system. The following table lists typical factors.

Factors Affecting Endothelium and NO Generation
age
gender
smoking
plasma cholesterol level
disease (especially coronary artery disease and peripheral vascular disorders)

With the acquisition of calibrated blood volume pulsatile data, researchers may identify other factors which affect the response of blood vessels and the endothelium during reactive hyperemia.

The following Physiological Process Table provides a general outline of the physiologic effects of reactive hyperemia on the endothelium and the cardiovascular system of a patient as currently understood by one of the inventors.

Physiological Process Table
1. cause anoxia or severe hypoxia in the limb's arterial system
2. which causes an increase in NO production by the arterial endothelium
3. which results in dilation of the local and distal arterial system
4. which is believed to cause a reduction in peripheral resistance in the resistive vessel muscles
5. which is generally believed to cause an increase in pulsatile blood flow (Q)
6. which causes a further increase (potentially) in pulsatile blood flow (Q) (which increase may be small or not measurable)

In summary, FIG. 6b shows the collapse of brachial artery 110 by blood pressure cuff 14. The illustrated force is shown by arrows 117. In a preferred embodiment, ischemia in the patient's limb is established for 5 minutes. In FIG. 6c, blood pressure cuff 14 has been quickly released and brachial artery 110 has expanded to diameter $d_2$. Even though significant suprasystolic pressure has been released from blood pressure cuff 14, pressure cuff 14 exerts a small pressure 119 (diastolic or near diastolic) on the limb 16 in order to capture physiological data regarding the pressure pulse waveforms at the predetermined diastolic pressure. Hence, force vector arrows 119 are smaller than vector arrows 117.

FIGS. 6a–6c are related to FIG. 5 in the following manner. Upon collapse the brachial artery 110 due to a suprasystolic pressure placed on region 112 about limb 16 of the patient, the downstream portions of the limb experience anoxia or severe hypoxia. When the suprasystolic pressure is released from the blood pressure cuff 14 (but maintained at or near diastolic pressure), there is a reduction in the peripheral resistance of the resistive blood vessel muscles 120 located in distal regions of the patient's limb, diagrammatically illustrated in FIG. 5. These resistive vessel muscles 120 are primarily located in and about the arterials 122. The relaxation of the resistive vessel muscles 120 causes an increase in pulsatile blood flow (identified herein as Q), and an increase in the generation and transmission of nitric oxide (NO) through the endothelium. This NO or chemical composition biomaker is generated throughout the endothelium and travels therethrough from arterials 122 upstream to a point about critical monitoring area 112 of brachial artery 110. The NO causes dilation of the arterial system primarily due to a relaxation of the resistive vessel muscles 120, an increase in pulsatile blood flow Q and a possible further increase in pulsatile blood flow. This last increase (step 6 in the Physiological Process Table) may not be measurable. However, it is apparent that a careful measurement of arterial blood vessels slightly upstream of the brachial arterial branch 114 (near the patient's elbow crease)

provides a very good indication of the health or the condition of the endothelium, the generation and transmission of NO and the health of the cardiovascular system during reactive hyperemia.

The present invention measures the production of NO and the condition of the blood vessel and endothelium about the entire limb 16 rather than simply measure the diameter of the brachial artery 110 as is currently done by ultrasound techniques.

The prior art systems utilizing ultrasonic imaging only focus on the change in diameter of brachial artery 110 during reactive hyperemia. This change in diameter $d_1$ to $d_2$ (FIGS. 6a, 6c) is on the order of 0.30 to 0.33 mm. Healthy patients without cardiovascular disease present an increase in brachial arterial diameter of approximately 6.2% during reactive hyperemia. Another group of patients having a history of coronary artery disease show an increase in brachial artery diameter of 1.3%. Accordingly, the sensitivity of the present invention, the ability of the present invention to automatically initiate a quick cuff release, and the standardization of the calibration pulse and the periodic calibration of the data acquisition system during the entire reactive hyperemia episode, all contribute to the benefits achieved by the present invention over the pre-existing technology. These benefits are apparent because of the small change (approximately 0.30 mm) of the brachial artery during reactive hyperemia. Other clinical studies using prior art technology have revealed that the response of the endothelium and the generation of NO can be directly correlated with the presence or absence of coronary artery disease. Since the present invention is a noninvasive method and system for detecting the onset and degree of coronary artery disease, the present invention is potentially better suited technically and practically than other invasive methods to detect coronary artery disease. Other invasive methods to detect these problems include cardiac catheterization and angiographic procedures.

Figure 7:
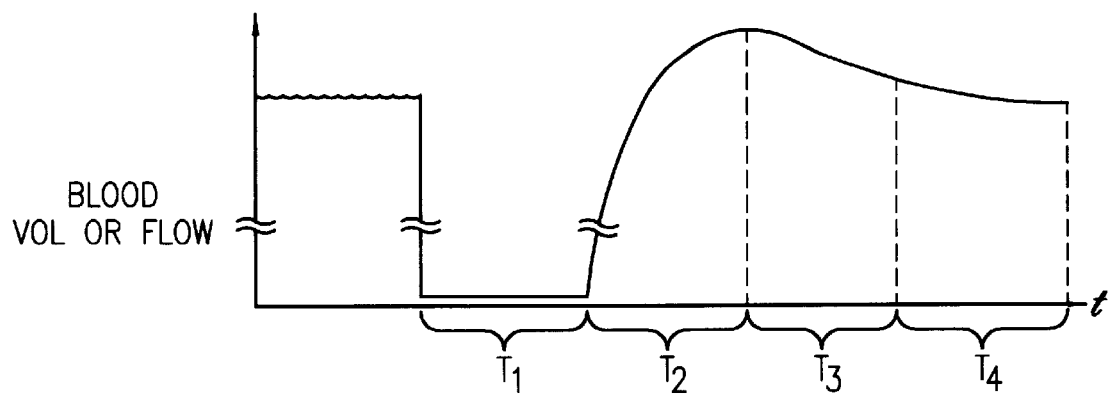
FIG. 7 diagrammatically illustrates a plot or graph of blood volume (V) or blood flow (Q) vs. time t which documents the reactive hyperemia episode in the patient's limb (time t may be illustrated in real time but not necessarily to scale)

FIG. 7 diagrammatically illustrates a plot or a chart of either blood volume V or blood flow Q versus time t. At time T1, the patient's limb is compressed and the limb experiences ischemia or extreme hypoxia (a 5 minute period). At time episodic period $T_2$, the system first initially quickly releases the pressure in blood pressure cuff 14, the pneumatic and electronic pressure sensing system settles to a predetermined diastolic pressure, the patient's limb and arterial system generates NO and provides initial stage data of the reactive hyperemic episode. Time period $T_2$ may last up to 1 minute. This is the first stage of the reaction. In time $T_3$, the system continues to measure the reactive hyperemia episode and detects the condition of the endothelium and the generation of NO through the cardiovascular system. The initial or primarily significant data acquisition period is the first 5 minutes after cuff pressure release ($T_2$ plus $T_3$). The subsequent 5 minute period $T_4$ captures the secondary phase data of the reactive hyperemia test (RHT Test).

| Reactive Hyperemic Time Table | |
|---|---|
| $T_1$ | five (5) minutes to achieve ischemia or extreme hypoxia |
| $T_2$ | about one (1) minute for physiological system to initiate first stage of reaction |
| $T_2$ plus $T_3$ | about five (5) minutes to monitor typical, primary phase of reactive hyperemia episode |
| $T_4$ | about five (5) minutes to monitor typical, secondary phase of reactive hyperemia episode |
| $T_2$ plus $T_3$ plus $T_4$ | about ten (10) minutes |

Utilizing ultrasound prior art techniques, the ultrasound operator, in the first minute after cuff release, visually identifies and locates the brachial artery and prepares himself or herself for the data acquisition imaging phase. In the subsequent 60 second period, the ultrasound operator captures the image of the greatest expansion of the diameter of the brachial artery. This image acquisition period generally corresponds to the peak of the blood flow waveform shown in FIG. 7. In the third 60 second period subsequent to cuff release, the operator watches the diameter of the brachial artery decrease. Since the diameter of the artery reduces in size, there is a decrease in blood flow. Of course, in the ultrasound data acquisition system, the operator only sees the change in arterial diameter (on the order of 0.30 mm). The ultrasound operator does not measure the change in blood flow. He or she measures arterial diameter change. However, this blood flow change is apparent in the sonic image because of the visually confirmed change in arterial diameter.

The present invention actually monitors and captures pressure pulse data and waveforms $P_t$ in real time and converts them to calibrated blood volume pulse data and waveforms $V_n$ with periodic calibration pulses. This direct measurement of blood volume V and blood flow (Q) is a significant difference between the ultrasound systems and the present invention.

Figure 8:
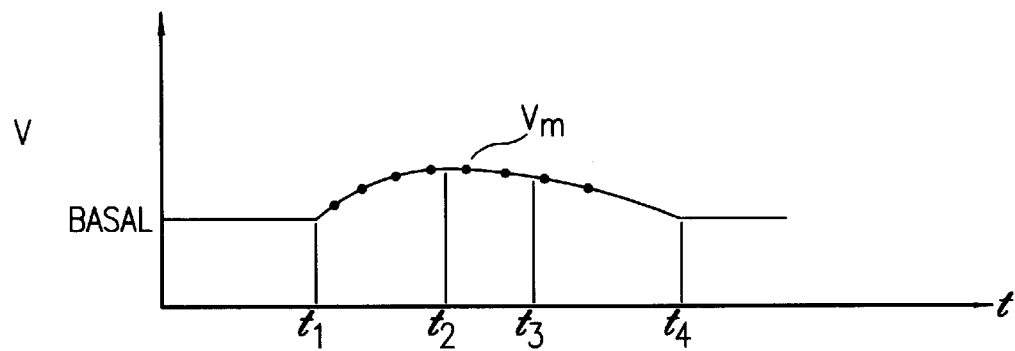
FIG. 8 diagrammatically illustrates a plot or graph of the pulsatile component of blood volume V during reactive hyperemia (with episodic time t being discontinuous)
Figure 9:
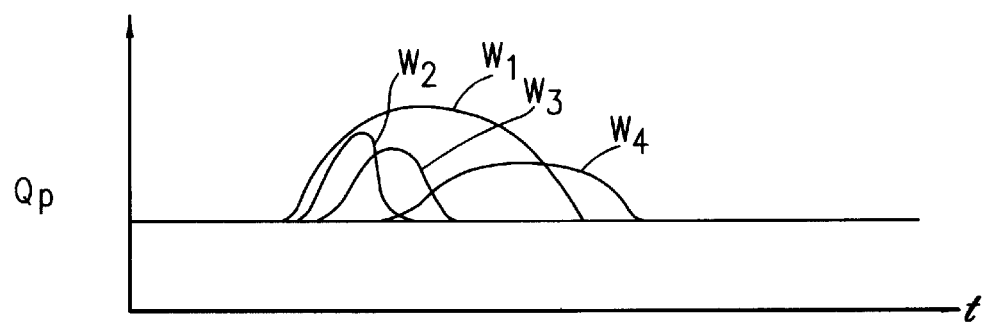
FIG. 9 diagrammatically illustrates blood flow Q (quantity versus time) and a number of waveform profiles showing a normal blood vessel flow and endothelial reaction after hyperemia (waveform $W_1$), a rapid recovery waveform profile ($W_2$), a diminished recovery waveform profile ($W_3$) and a diminished and prolonged recovery waveform profile ($W_4$) which indicates various coronary arterial conditions and diseased states and vascular conditions and problems as compared with the normal waveform profile ($W_1$)

FIG. 8 diagrammatically illustrates a plot or a graph of the pulsatile component of blood flow $Q_p$ versus episode time t. Essentially, the present invention captures pressure waveform $P_t$ data, converts that pressure waveform data into blood volume pulse $V_n$ data (per a calibration routine) and then, in one embodiment, samples periodic blood volume data (preferably obtaining the maximum or peak value $V_m$ of selected, periodic waves $V_n$). The peak value of blood volume $V_m$ in relation to episodic time is one type of measurement to show the condition of the blood vessel. Another measurement is the resulting calculation of pulsatile blood flow $Q_p$. FIG. 9 is blood flow plotted data. In this embodiment in FIG. 8, the height or peak m of the blood volume pulsatile signal V is plotted versus episode time t. At time $t_1$, the blood pressure cuff has been released, the system is settled (about 20 seconds) and data acquisition begins. A settling period may be necessary due to the pneumatic quick release of air pressure. A plurality of blood volume peak data points $V_m$ are obtained and plotted and mapped. Mapping may be to a data table ($V_m$ and episodic time) or graphically stored ($V_m$ versus t). At time $t_2$, the maximum blood volume peak $V_m$ is computed by the system and preferably displayed to the operator, health professional or physician. At time $t_3$, the patient's cardiovascular system has reached the end of the reactive hyperemia episode.

In FIG. 8, the plot of $V_m$ with respect to time t may not be absolutely precise. The reactive episodic time t may be replaced by pulse wave number n. In other words if the patient has a heart rate of 60 beats per minute and the test lasts 3 minutes (a short version of the test), 180 blood pressure waves or data are available. The signal settle period may be one minute. Sixty (60) waves are discarded at initial settling stage period $T_1$. As explained later, six (6) wave cycles are utilized for each calibration window or cycle. As an alternative embodiment, three (3) of the six waves in each calibration window are averaged to reduce motion artifacts. In one initial working embodiment, only one wave or data value from each calibration cycle is initially utilized. Accordingly from the 120 wave segment (180 waves less 60 waves for signal settling), 20 corrected wave signals or data $V_n$ are available. The peak values $V_m$ are computed. Since the patient's heart rate may not be precisely 60 beats per minute (it may be 59, 62, 58), the system may plot $V_m$ versus pressure or volume wave number 61, 67, 74, 81, 88, 95. . . etc. In a working embodiment, $V_m$ versus episodic time is mapped to a data table and to a graphic, waveform display. Blood flow $Q_p$ is calculated by (a) integrating the $V_n$ pulsatile waveform with respect to time (after the signal settling period), adding the integrated signal data and dividing the sum by a standard time period (the result being flow $Q_p$ in ml per minute).

However, FIG. 8 is accurate with respect to blood volume flow $Q_p$ versus episodic time t if time t is measured from the quick cuff release time. In this event, there is a "discontinuity" in the graph because the graph in FIG. 8 does not show ischemia time $T_1$ (FIG. 7). Further, time $t_1$ begins at time period $T_2$ in FIG. 7. Time is also discontinuous in FIG. 7. Since the physician or health professional is primarily interested in the $V_m$ data and the shape, height, size and other waveform characteristics of $V_m$ from time $t_1$ to time $t_3$ and the time $t_4$, the time-based discontinuity due to ischemia is not significant. If wave number is used rather than time, no discontinuity would be present.

With respect to FIG. 8, a basal blood flow level $Q_p$ has been established based upon the calibrated and summed blood volume pulsatile data. This basal level is obtained prior to initiating a reactive hyperemia in the patient's limb. The basal blood volume level is also obtained electronically prior to the test. $V_m$ is the peak value of the corrected blood volume pulse wave $V_n$ at predetermined times. In an initial working embodiment, five $V_m$ data points are acquired, calibrated, processed and calculated from the pulsatile pressure wave data during the 60 second period after a 20 second signal settlement period (after $t_1$). The signal settlement period may be adjusted as necessary to match equipment limitations. Shorter settle periods are preferred. An additional seven $V_m$ data points or values are obtained and processed during the remaining portion of the five minute reactive hyperemia test (short RHT test). For example, $V_m$ data is obtained at about 110 seconds after release, at 140 seconds, 170 seconds, 200 seconds, 230 seconds, 260 seconds, and 290 seconds after release of $t_1$ (FIG. 8). Data tables for $V_m$ at those times are mapped electronically by waveform data acquisition and processing techniques.

In FIG. 9, the pulsatile component of blood flow $Q_p$ versus episodic time t for several patients is plotted atop each other. Essentially, FIGS. 8 and 9 show individual and collective recovery profiles for reactive hyperemia tests, respectively. These recovery profiles or recovery waveforms W provide good physiological data regarding the health or the condition of the endothelium, the generation of NO by the patient and the cardiovascular health of the patient.

Ultrasound studies have established that if patients with cardiovascular disease utilize nitroglycerin, this increases NO in the patient's system and the expansion of the brachial arterial diameter during reactive hyperemia changes from 3.78 mm to 3.89 mm. Accordingly, the recovery profile waveforms in FIGS. 8 and 9 also provide an indication of the effectiveness of drugs, e.g. nitroglycerin, in the patient as well as the generation of NO and the transmission of NO through the arterial bed.

It has been proposed, based upon the present invention, that the recovery waveform profiles $w_1$, $w_2$, $w_3$ and $w_4$ shown in FIG. 9 mostly likely show a normal state (waveform $w_1$), a rapid recovery (waveform $w_2$), a diminished recovery (waveform $w_3$), and a diminished prolonged recovery (waveform $w_4$). Of course, deviations or changes from the normal recovery profile waveform $w_1$ provide an indication of the health and condition of the cardiovascular system of the patient under study.

| Exemplary Waveform Classification Table | |
|---|---|
| $W_1$ | normal recovery profile |
| $W_2$ | rapid recovery |
| $W_3$ | diminished recovery |
| $W_4$ | diminished and prolonged recovery |

Further, the recovery profile waveform may be analyzed with various mathematical algorithms. For example, the researcher could compare the sequential calibrated blood volume pulse waveform $V_n$ at 30 second intervals after signal settlement period (for a 3 minute reactive hyperemia episode, 6 blood volume pulse waveforms $V_n$ are studied inclusive of initial stage $T_1$ but after signal settlement) and review the rise and fall of the peak values $V_m$ for the six waveforms. Running averages of blood volume pulse waveforms (e.g. computing a three (3) wave average $V_n$-Ave during successive six wave calibration periods) could be taken and compared against each other. The researcher could average three waveforms $V_n$-Ave prior to the calibration pulse (in a six wave calibration cycle) and analyze the running peak values $V_m$-Ave over the 3–5 minute reactive hyperemia episode. Further, the waveforms could be utilized with weighted average (based on time t from initial stage $T_1$) to compare the blood volume data $V_m$ with respect to episodic time. Blood flow $Q_p$ at different episodic times may be compared. The following Waveform Analysis Table may provide some guidance.

| Waveform Analysis Table |
|---|
| periodic, selected peak values or data $V_m$ |
| running average peak values, e.g., average 3 $V_m$ ($V_m$ - Ave) episode analysis, use $V_m$ – Ave as data points $V_t$, $V_{t2}$, $V_{t3}$, $V_{tn}$ |
| weighted average calculations of $V_{tn}$ based on time of acquisition |
| leading slope of $V_{tn}$ (or trailing slope) at selected episodic times $t_1$ $t_2$ |
| leading slope $V_{rm}$ or $Q_p$ (or trailing slope) during episode |
| gross value of slope (peak $V_m$ or $Q_p$ versus time from base to peak ($t_1$–$t_2$)) |
| integrated value of corrected $V_a$ waveform (from $t_{1F}$ to $t_{1B}$) (FIG. 10) |
| integrated value of $V_m$ and/or $Q_p$ waveform (FIG. 8) |
| first, second or third derivatives of $V_m$ waveform or $Q_p$ at selected episode times. |

Figure 10:
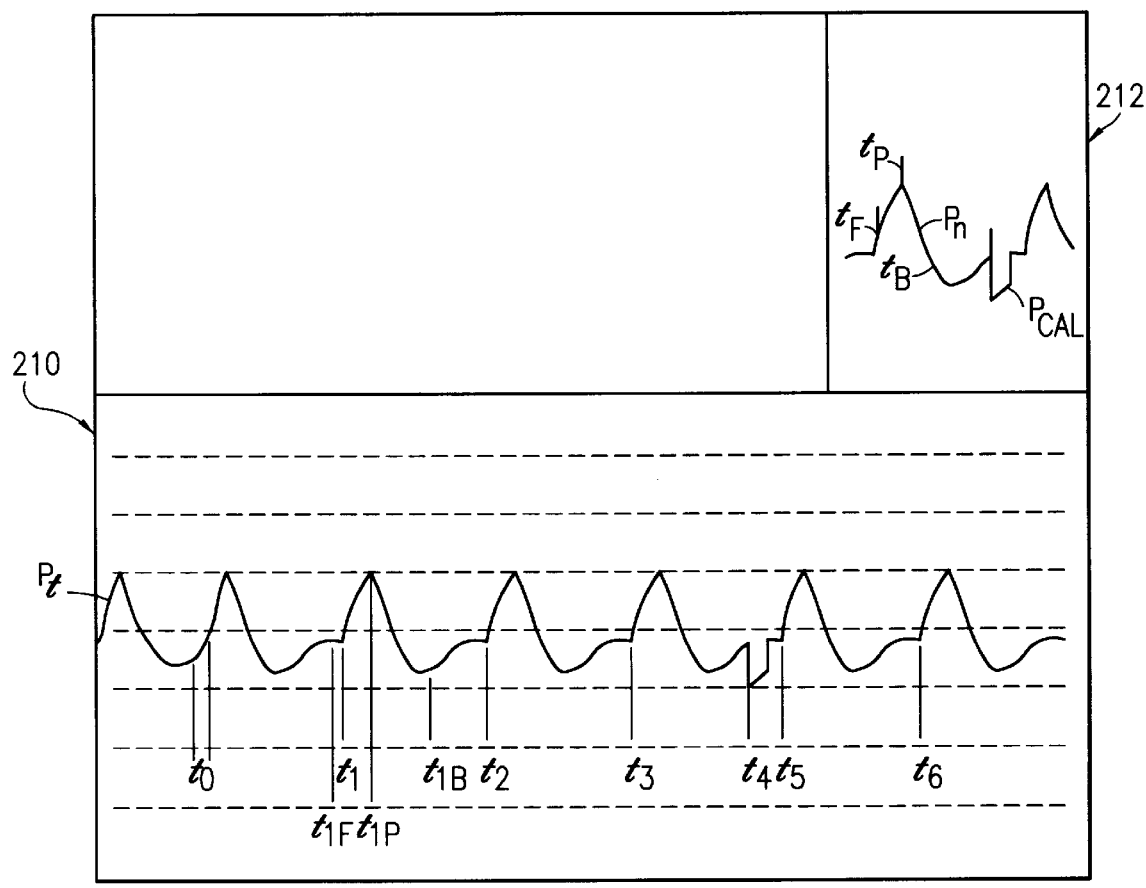
FIG. 10 diagrammatically illustrates a plurality detected pressure pulse waveforms $P_t$, the resultant calibration pulse ($t_4$) and further diagrammatically illustrates the pressure pulse waveform $P_n$ in accordance with the principles of the present invention.

FIG. 10 diagrammatically illustrates one method for calibrating the blood pressure pulse wave $P_r$ and generating and calculating blood volume pulse waveform $V_n$.

In lower region 210, the system displays (on a monitor) pressure pulse waveforms $P_r$. At a time prior to $t_0$, the system experiences discontinuities and transients due to pneumatic and electronic settlement based on the quick release of pressure from blood pressure cuff 14. A 20 second signal settlement period is used in a working embodiment. Subsequent to time $t_0$, the system begins monitoring the waveforms P at $t_1$, $t_2$, $t_3$, and particularly the system detects the foot of the wave at $t_{1f}$, the peak of the wave at $t_{1p}$, and the base of the wave at $t_{1b}$.

This detection of wave features is done by standard mathematical algorithms analyzing the waves during real time acquisition of data, that is, the pressure pulse waveform P. First, second and third derivatives of the acquired data signal may be utilized to locate waveform features. In the embodiment shown in FIG. 10, the system determines when three substantial identical pressure pulse waveforms $P_t$ have been received (based on peak height or integrated valve or otherwise) and then, after predetermined time period from detecting the initial slope of the third waveform at $t_3$, the system generates a calibration pneumatic pulse $V_{cc}$ at time $t_4$. The calibration volume $V_{cc}$ may be triggered by detecting and counting other waveform features.

As described earlier in connection with the preferred embodiment, this volume change is achieved by cylinder head moving and expanding chamber 68 a predetermined amount $V_{cc}$ See FIG. 2. This predetermined volume $V_{cc}$ is added to the pneumatic system and generates a measurable change in the pressure signal which is the calibration pressure pulse $P_{cal}$. The system then computes the actual blood volume pulse $V_n$ in accordance with the following equation.

$$V_n \text{ divided by } P_{dia} \text{ equals Vcc divided by } P_{cal}. \qquad \text{Eq. 3}$$

The calibrated and measured blood volume pulse waveform $V_n$ is obtained by multiplying the measured or pre-set diastolic pressure $P_{dia}$ by the ratio of the $V_{cc}$ and $p_{cal}$. The calibration volume $V_{cc}$ is currently 0.68 ml but may be set at 1 ml. Accordingly in display region 212, the system displays the recorded pressure wave $P_n$. Alternatively, the system may display the measured and corrected blood volume pulse waveform $V_n$. In this situation, there is a time-based discontinuity in the display due to the signal processing of $V_n$ with $P_{cal}$. Additionally, the system may illustrate the calibration pulse $P_{cal}$.

Subsequent to the calibration pulse at time $t_4$, the pneumatic and electronic system may require a one or two wave period to settle in order to remove any transients caused by the calibration pulse $V_{cc}$. The system ignores this second plurality of pressure waves at $t_5$ and $t_6$ in the calibration cycle.

Figure 11:
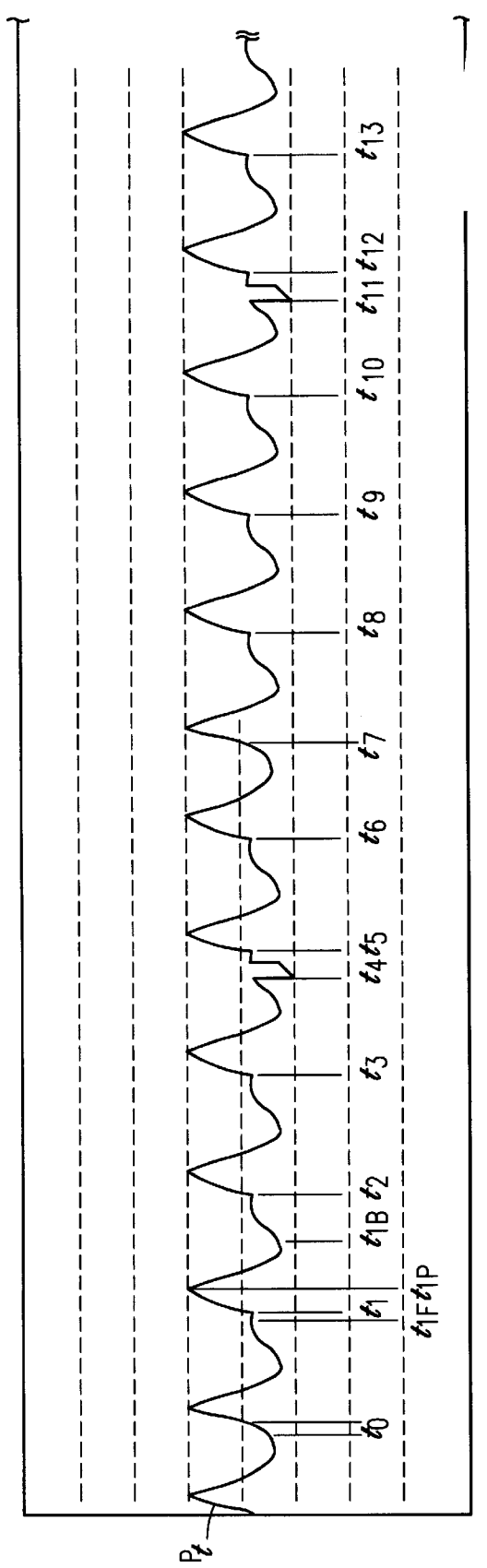
FIG. 11 diagrammatically illustrates a plurality of pressure pulse waveforms $P_t$ and a periodic calibration pulse for the pressure waveforms in accordance with the principles of the present invention.

In FIG. 11, one embodiment of the present system is illustrated. In FIG. 11, the calibration pulses are generated at times $t_4$ and $t_{11}$ during a six cycle calibration period. In other words, the system acquires and records, in real time, pressure pulse waveforms P at times $t_1$, $t_2$ and $t_3$, fires a calibration pulse $V_{cc}$ after waveform at $t_3$ (calibration at time $t_4$), enables the system to settle with waveforms P at times $t_5$, $t_6$ and time $t_7$ (which post-calibration waveform data may be discarded), then acquires and records the next three pressure pulse waveforms P at times $t_8$, $t_9$ and $t_{10}$ and subsequently fires a calibration volume $V_{cc}$ at time $t_{11}$ into the system. Therefore, the calibration pulse is issued during a six pressure pulse waveform cycle, the system discards three subsequent post-calibration pressure pulse waveforms and saves and records the previous three pressure pulse waveforms immediately prior to the calibration pulse. Of course the system may record all pressure pulse waveform data but only utilize one, two or three pre-calibration waves to calculate data point $V_m$ in each calibration cycle per FIG. 8. The currently preferred embodiment records 12, five second strips of data during the long, ten minute RHT test.

If the initial, critical data period for the reactive hyperemia episode lasts 5 minutes and if the patient's heart beats 60 beats per minute, 300 pressure pulse waveforms are acquired, 20 are discarded during the quick release signal settlement period (20 seconds) about 140 pressure pulse waveforms are discarded in the post calibration cycles, and about 140 are available for processing as calibrated blood volume pulse waveforms data $V_n$ in the method and system. This data provides approximately 140 potentially available data points $V_m$ and computation plot $Q_p$ versus episodic time shown in FIG. 8.

Figure 12A:
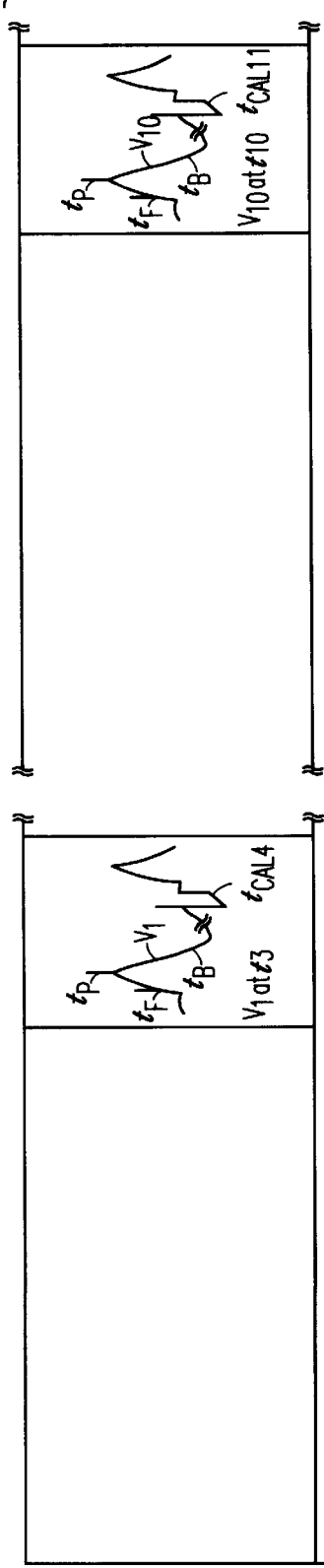
FIGS. 12a, and 12b diagrammatically illustrate the system capturing a large plurality of pressure wave forms $P_t$, several periodic calibration pulses or cycles and the computation and illustration of blood volume waveforms $V_n$ at various times during the reactive hyperemia episode.
Figure 12A:
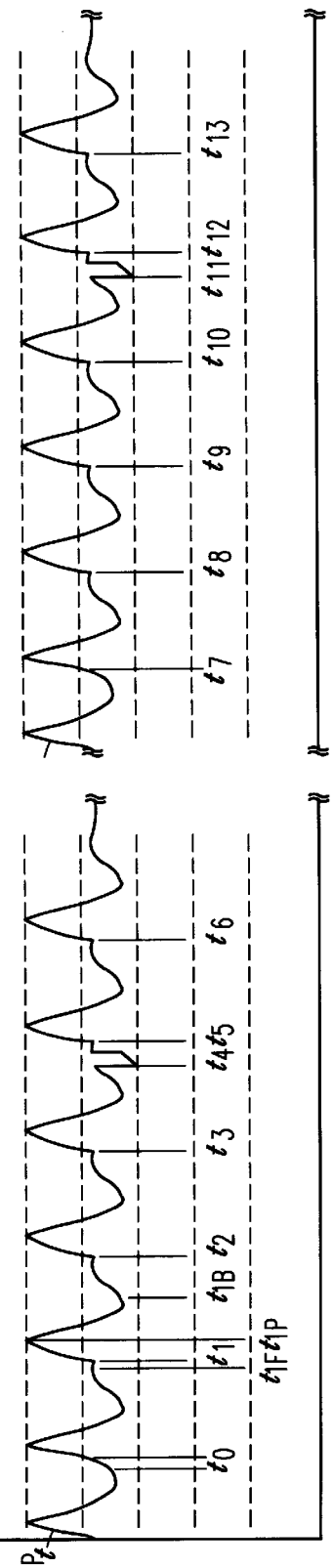
Figure 12B:
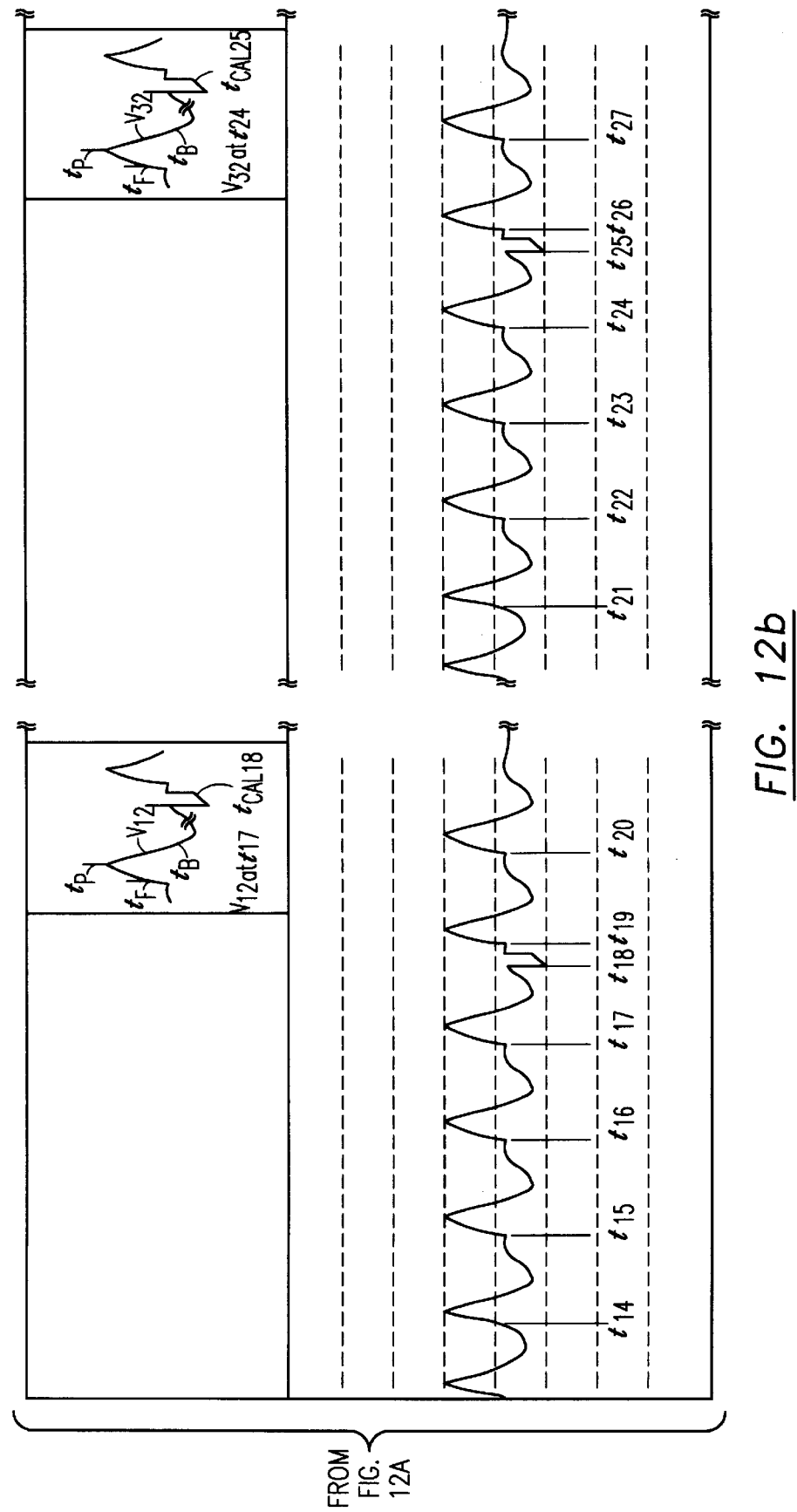

FIGS. 12*a*–12*b* diagrammatically show the decreasing pulse height for the pressure pulse waveforms $P_r$. The following Exemplary Timing Table describes FIGS. 12*a*–12*b*.

| Exemplary Timing Table | |
| --- | --- |
| $t < t_o$ | prior to $t_o$, system is subject to transients due to the quick cuff release and is unstable and unsettled |
| $t_o$ | system is settled and wave counter started, record waveform function ON |
| $t_1$ to $t_3$ | three (3) generally similar pressure waves $P_t$ identified |
| $t_{1F}$ | foot of waveform $P_1$ at $t_1$ |
| $t_1$ | waveform marker and wave count N incremented |
| $t_{1P}$ | peak of waveform $P_1$ |
| $t_{1B}$ | base of waveform $P_1$ |
| $t_2$ | waveform $P_2$ detected and wave count N incremented |
| $t_3$ | waveform $P_3$ detected and counted |
| $t_4$ | calibration volume change $V_{cc}$ - system measures pressure change $P_{CAL}$ due to calibration change $V_{cc}$ -- system computes blood volume waveform $V_n$ based on calibration -- displays $V_n$ or $P_n$ |
| $t_5$–$t_6$ | system settles and recovers from calibration event |
| $t_8$–$t_{10}$ | system confirms three (3) generally similar pressure waves P at $t_8$, $t_9$ and $t_{10}$ |
| $t_{11}$ | calibration event -- system computes the tenth blood volume data point $V_{10}$ based on calibration event at $t_{11}$ and waveform P at $t_{10}$ -- note this assumes system captured and calibrated $V_1$, $V_2$, $V_3$, ... $V_9$ during 9 $P_t$ waves where r is number of P waveforms per calibration cycle |
| $t_{15}$–$t_{17}$ | system confirms three good P waves |
| $t_{18}$ | calibration event - compute and display $V_{12}$ based on calibration $t_{18}$ and P at $t_{17}$ |
| $t_{22}$–$t_{24}$ | confirm similar waveforms |
| $t_{25}$ | calibrate and compute $V_{32}$ with cal pulse $t_{25}$ and P at $t_{24}$ -- display |

The signal processing routines described herein may be changed. For example, to obtain an average blood volume pulse waveform $V_n$-Ave, the embodiment locates a common waveform feature on each wave, e.g. the leading edge (first derivative and slope detection), and overlays multiple, predetermined waveforms atop each other. Another averaging technique includes computing the peak value $V_m$, then averaging a predetermined number of peak values together to obtain $V_m$-Ave. The averaging may be done on pressure waves P prior to calculating blood volume V. In the calibration routine, other calibration windows or cycles may be utilized. Herein, a six (6) waveform cycle is utilized. However, a four (4) or a ten (10) correction and calibration cycle may be appropriate. Further, rather than using a three (3) wave average, a six (6) wave average may be appropriate.

With respect to the wave number and episodic time charts in FIGS. 8 and 9, if a six (6) wave calibration cycle is selected and a three (3) wave average is utilized (using waveform overlays as the averaging algorithm), the system counts the wave numbers N to track the calibration cycles and to compute $V_n$-Ave as processed signal overlays. A correlation between episodic time and wave count is maintained by the processor and memory. Additionally, the computerized system starts a timer at the initial state $T_2$ (FIG. 7) and keeps a running list or map of the wave number N and the episodic time ($t_1$ $t_2$ $t_3$ $t_4$ in FIG. 8). After calibrating with six (6) wave cycles for five (5) minutes, correcting the pressure pulse waves $P_n$ and obtaining blood volume pulse waves $V_n$, averaging to obtain $V_n$-Ave, and calculating averaged peak values $V_m$-Ave, the resulting 50 data points $V_m$-Ave are then mapped to the corresponding reactive hyperemia episodic time with the stored time versus waveform number N. The system plots $V_m$-Ave versus episodic time t as waveforms shown in FIGS. 8 and 9. The system also maps a data table with the averaged peak and episodic time. The episodic time may be at selected $t_1 f$ or t b or at calibration time $t_4$ for each calibration cycle. See FIG. 10, waveform base, foot, peak or trailing base. Other episodic time markers may be selected.

The display routines may also be modified from those described and illustrated above. For example, rather than display blood pressure pulse $P_n$ in display window 212 of FIG. 10, FIGS. 12a and 12b show the corrected and computed blood volume pulsatile waveform $V_n$. If blood volume wave $V_n$ is illustrated, the displayed wave will have a time discontinuity between the inverted V-shaped wave $V_n$ and the measured calibration pressure pulse (a negative waveform) $P_{cal}$. Basically $V_n$ is a computed value from $P_n$ as corrected by the ratio $V_{cc}$ versus $P_{cal}$.

Further, the system may sequentially show acquired and processed signals after the signal settle time frame (20 sec.) as follows: $P_n$ with $P_{cal}$ for 30 sec.; initial $V_n$ waves at episodic times 32 seconds, 44 seconds, 56 seconds, 68 seconds, 80 seconds, 92 seconds (the first "clear data acquisition" time frame 60 sec. episodic period); secondary $V_n$ at about episodic times 122 seconds, 152 seconds (a $V_n$ data waveform in the second 60 sec. episodic clear time frame period); tertiary $V_n$ at about episodic times 182 seconds, 212 seconds, 302 seconds and 332 seconds ($V_n$ data wave in the third 60 sec. episodic clear time period); the fourth and fifth $V_n$ representing fourth and fifth episodic periods; and blood flow $Q_p$ versus episodic time t (FIG. 8) for 60 sec. during or after reactive hyperemia test. Of course, blood flow $Q_p$ versus episodic time t is both a data table and a waveform plot of 50 data points computed from V waves during real time acquisition period $T_2$ and $T_3$ and $t_4$ (FIG. 7).

Also, the computer system generates electronic and print versions of the reactive hyperemic test results as necessary.

Blood volume and blood flow both characterize the condition of the patient's arterial system, the condition of the endothelium, the generation and transmission of NO and the action of drugs on those biological systems. Blood flow is a volumetric quantity of blood with respect to time. Typically, blood volume is measured in ml per minute. Blood flow is mathematically obtained from the $V_n$ waveform correlated to time. "Pulsatile" refers to the "pulse" caused by the heart pumping blood through the system. "Pulsatile" refers to the signal, flow or volume in excess of the basal value or rate. Waveform data is relatively easily converted into a data table once a constant time period has been selected. Similarly, data from a time based and mapped table can be reformatted as a wave or other time-based presentational display or print-out. "Mapping" involves the step or function of correlating data valves to a certain time frame and time period data. "Mapping" occurs both in a data table and a waveform illustration.

In an initial working embodiment, the system operates as follows:

Exemplary Process Table

1. Gather and store patient data and risk profile data
2. Obtain brachial BP when the patient is supine (e.g. 120/80)
3. Inflate cuff to slightly less than diastolic pressure (80−5=75 mmHg)
4. System calibrates, measures and stores base line P, V, $V_m$ and $Q_p$
5. Inflate cuff to suprastolic (120+20=140 mmHg)
6. Occlude arterial system for five (5) minutes
7. Quickly deflate to slightly less than diastolic pressure (80−5=75 mmHg)
8. Let electronic and pneumatic system settle (about 20 seconds)
9. Periodically calibrate, measure $P_n$ and $V_n$ and calculate $V_m$ and $Q_p$ data points (about 5 data point acquisitions and computations) for primary episodic data acquisition time (first 60 seconds). Store data. Display as necessary. Correlate to episodic time.
10. Repeat step 9 for remaining four (4) minutes of the short reactive hyperemic test (short RHT). Gather and calculate seven or eight additional data points $V_m$ and $Q_p$ (based on $P_n$ and $V_n$) over the test period.
11. Generate data table $V_m$ versus episodic time and $Q_p$ versus t. Print-out. Plot graph. Display. Print-out.
12. Generate comparison data table with healthy RHT waves and data. Repeat with waveform.

In a further enhancement, a carefully manufactured bellows with a predetermined volumetric size may be used rather that cylinder piston system 60.

In a subsequent working embodiment (the currently preferred embodiment, subject to revision following a plurality of patent studies), the system operates as follows:

Exemplary Process Table (Revised)

1. Gather and store patient data and risk profile data. Display upon entry into system.
2. Obtain brachial BP when the patient is supine (e.g. 120/80) by traditional methods.
3. Start test. Inflate cuff to slightly less than diastolic pressure (80−5=75 mmHg).
4. System calibrates, measures and stores base line P, V, $V_m$ and $Q_p$ Display.
5. Inflate cuff to suprastolic (120+20=140 mmHg) via machine.
6. Occlude arterial system for five (5) minutes. Display and possibly audibly announce a five minute countdown to cuff/pressure release. Provide early warning to patient immediately prior to cuff pressure release, "Do not move during RHT test."
7. Quickly deflate cuff to slightly less than diastolic pressure (80−5=75 mmHg).
8. Let electronic and pneumatic system settle (about 20 seconds).
9. Capture data. Periodically calibrate, measure $P_n$ and $V_n$ and calculate $V_m$ and $Q_p$ data points (average j number of signals to obtain e number of averaged signals during predefined time segment (quintiles) during 5 min. short test or 10 min. long RHT test. See Phase Process Table below for values of j and e) for primary episodic "clear data acquisition" time (subsequent to the 20 sec. signal settle time). Store data. Display as necessary. Correlate to episodic time. Display.
10. Repeat step 9 for remaining test period (10 min. test) Gather and calculate data points $V_m$ and $Q_p$ (based on $P_n$ and $V_n$) over the test period. Calculate Qp (ratio); Qp (phase); $V_m$ (ratio); $V_m$ (phase); and V (exp))explained below).
11. Generate data table $V_m$ versus episodic time and $Q_p$ versus t. Print-out. Plot graph. Display. Print-out.
12. Generate comparison data table with healthy RHT waveform or data. Repeat with waveform.

Figure 13:
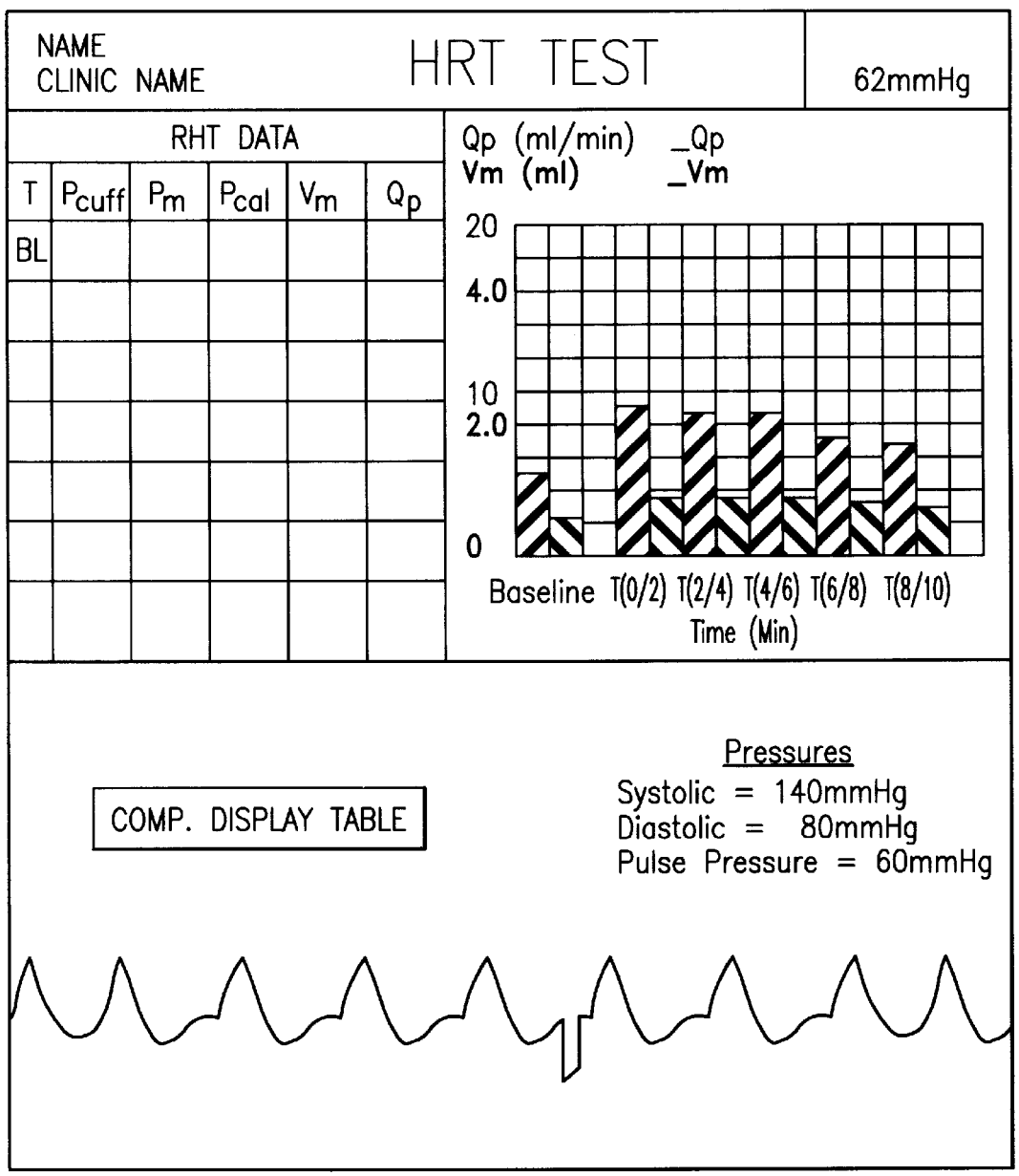
FIG. 13 diagrammatically illustrates one configuration of a user interface display.

One configuration of the user interface for present invention is diagrammatically illustrated in FIG. 13. This display shows the name of the patient, the name of the clinic or doctor conducting the test, and the current pressure reading from the pneumatic system in the upper horizontal region of the interface. Beneath this information bar is a data table (on the left-hand side) and a bar chart (on the right) showing the results of the test. During the test, portions of this data and bar chart are displayed such that the technician conducting the test obtains real-time feedback regarding the quality and quantity of data captured by the system. Beneath the RHT Test Data Table is a computational table, a display showing blood pressure data and the real time waveform display of pressure pulsatile signals (with a calibration pulse therein).

| RHT DATA TABLE (SHORT RHT TEST) (abbreviated) | | | | | |
|---|---|---|---|---|---|
| Time (min) | Pcuff | Pm | Pcal | Vm | Qp |
| Baseline | 68 | 1.05 | 1.29 | 0.53 | 4.69 |
| 0.3 | 79 | 1.75 | 1.39 | 0.82 | 9.06 |
| 0.5 | 77 | 1.85 | 1.37 | 0.88 | 8.95 |
| 0.7 | 78 | 1.90 | 1.38 | 0.90 | 8.71 |
| 0.9 | 75 | 1.83 | 1.35 | 0.88 | 8.22 |
| 1.1 | 76 | 1.91 | 1.36 | 0.91 | 8.59 |
| 1.4 | 76 | 1.93 | 1.36 | 0.92 | 8.58 |
| 1.7 | 76 | 1.84 | 1.36 | 0.88 | 8.56 |
| 2.1 | 79 | 1.79 | 1.39 | 0.84 | 6.68 |
| 2.6 | 74 | 1.66 | 1.34 | 0.80 | 7.97 |
| 3.1 | 78 | 1.76 | 1.38 | 0.83 | 8.00 |
| 3.6 | 73 | 1.24 | 1.33 | 0.60 | 6.32 |

In addition to the tabular display of the RHT Data Table, the system, in a current embodiment, displays the following computations shown below in the Computational Display Table.

Computational Display Table

Qp Max Ratio=1.90 T (0–2 min) ($1^{st}$ quintile)

Vm Max Ratio=1.70 T (4–6 min) ($3^{rd}$ quintile)

V(Exp)=33.88 ml

The computational display includes the variables set forth below.

Variable Table

Qp Max Ratio [a label]=x T (y min) (z quintile)

where x=blood flow maximum value in ml per minute;

where y=the time frame corresponding to max. blood flow Qp; and, where z=the quintile corresponding to max. blood flow Qp.

Vm Max Ratio [a label]=r T (n min) (u quintile)

where r=blood volume maximum value in cc;

where n=the time frame corresponding to max. blood volume Vm; and, where u=the quintile corresponding to max. blood volume Vm.

V(Exp) [a label]=k ml.

where k=computational value of total blood volume measured during the entire RHT test (whether 5 min. (short test) or 10 min. (long test)).

The RHT test may measure and monitor reactive hyperemia for the initial five (5) minutes of the hyperemic episode (typically capturing primary phase RHT data) or may measure and monitor reactive hyperemia for the full ten (10) minutes of the hyperemic episode. Researches do not have sufficient information at this time to determine the exact length of the RHT test. In any event, the operational aspects of the RHT test are substantially similar. Multiple and frequent calibrations are taken to gather and correct the raw blood pressure pulse data and compute blood volume pulsatile data and flow. The theories described herein are applicable to RHT tests ranging from at least three (3) minutes subsequent to the quick release of the suprasystolic cuff pressure to about ten (10) minutes post cuff pressure release. The claims appended hereto are meant to cover these test time frames.

The following Phase Process Table refers to a long, ten (10) minute RHT test wherein the 10 minute data acquisition period is subdivided into fifths or quintiles. Other data acquisition segments may be established following clinical evaluations of a reasonable number of patients. The term "phase" refers to the time or episodic time of data acquisition.

| PHASE PROCESS TABLE (LONG RHT TEST) | | |
|---|---|---|
| RHT Testing Phase | Measurement Time | Plotted Value (Qp and Vm) |
| BL | Baseline | Baseline |
| T (0–2 min) ($1^{st}$ quintile) | 0.5 min, 1 min 2 min | Average (3 measurements) |
| T (2–4 min) ($2^{nd}$ quintile) | 3 min, 4 min | Average (2 measurements) |
| T (4–6 min) ($3^{rd}$ quintile) | 5 min, 6 min | Average (2 measurements) |
| T (6–8 min) ($4^{th}$ quintile) | 7 min, 8 min | Average (2 measurements) |
| T (8–10 min) ($5^{th}$ quintile) | 9 min, 10 min | Average (2 measurements) |

The blood volume signals or the raw pressure pulse signals are averaged in this currently preferred embodiment of the invention. Averaging (a) reduces involuntary motion artifact corruption of the data (large movement by the patient requires electronic signal processing to detect and block-out or ignore the resulting signals which are aberrations of the true pressure pulse signals); and (b) smooths the signals. Data values may be averaged or waveform data may be averaged. In the currently preferred embodiment of the invention, wave peak data values are averaged. Mathematically, it does not matter whether pressure pulse data values or blood volume peak data values are averaged. Other averaging factors (rather than the 3 point and 2 point average) may be utilized. However, the time based accuracy of the pulsatile data deteriorates if higher averaging values are utilized by the data acquisition system.

The Computational Display Table shown and described above is obtained from the following computations:

$$Qp(Ratio) = Qp(Max)/Qp(BL(baseline)). \quad \text{Eq. 4}$$

$$Qp(Phase(time\ of\ occurence)) = 1^{st}, 2^{nd}, 3^{rd}, 4^{th}, 5^{th} \quad \text{Eq. 5}$$
$$\text{period where } 1^{st} = T(0-2\ \text{min}) \text{ etc.}$$
$$\text{and where } Qp\ max.\ \text{is found.}$$

$$Vm(Ratio) = Vm(max)/Vm(BL) \quad \text{Eq. 6}$$

$$Vm(Phase) = 1^{st}, 2^{nd}, 3^{rd}, 4^{th}, 5^{th} \text{quintile time periods} \quad \text{Eq. 7}$$

$$V(Exp) = ((Qp(1^{st}) \times 2) + (Qp(2^{nd}) \times 2) + (Qp(3^{rd}) \times 2) + \quad \text{Eq. 8}$$
$$(Qp(4^{th}) \times 2) + (Qp(5\text{th}) \times 2) - Qp(BL)) \times 10\ \text{min}.$$

The last formula for V (exp) refers to blood volume expansion or the capacitive value of the arterial system. During reactive hyperemia, the arterial system expands, captures a greater amount of blood volume than normally and temporarily stores that blood volume. This is similar to a capacitor which stores electrical energy for a time. In the arterial system, this stored, excess blood volume is dissipated over time from the peak or maximum value Vmax. The total blood volume generated, captured, stored and dissipated during the entire reactive hyperemic episode is indicative of the health and physiologic characteristic of the arterial system and the endothelium. At the present time, researchers do not know whether the phase of the signal (a time based analysis) or a total flow or volume or a combination of this data is most significant.

The present working embodiment utilizes a ten minute test period after the five minute occlusion period. The episodic test period is divided into six (6) testing phases. To generate the aforementioned data, the electronic system electronically stores signals representing 12, five second strips of pressure waveforms. If necessary, the electronic system could store waveform signals for the entire 10 minute episodic test period. Simple data processing techniques are utilized herein due to the novelty of the test in the medical community.

An important advantage of the present invention is the simplicity of operation. The technician asks the patient a series of simple questions (Do you smoke cigarettes? etc.), inputs the data into the system, takes the blood pressure of the patient by conventional methods, records this BP data into the system, wraps the cuff around the patient's arm, and presses a START key. The system thereafter operates in an automatic fashion.

FIG. 13 also illustrates the baseline (BL) maximum blood volume Vm (ml), and the basal blood flow Qp (ml/min). In the current, revised working embodiment, the RHT test is divided into quintiles. Maximum blood volume Vm (averaged) and blood flow is shown in each quintile with a bar graph. An important data comparison feature is the difference between the baseline values and the values in each quintile. The display may be altered to show differences rather than actual values. Also, the bar graph may be replaced with a waveform display. The waveform may be generated by datapoints at the top of each bar in the bar graph plot. A waveform smoothing routine may be used to better illustrate the compiled data.

The claims appended hereto are meant to cover modification and changes within the scope and spirit of the present invention.

What is claimed is:

1. A calibrated method for characterizing blood flow in a limb of a patient during reactive hyperemia with a blood pressure cuff bound about said limb comprising the steps of:

establishing a predetermined, near diastolic, pressure in said blood pressure cuff during the reactive hyperemic episode;

substantially continually sensing the pressure in said blood pressure cuff during the reactive hyperemic episode;

during the reactive hyperemic episode, periodically changing a volume of said blood pressure cuff by a predetermined volumetric amount and substantially concurrently sensing a resultant change in the pressure as a calibration pressure pulse;

calculating pulsatile blood volume by correcting the sensed pressure with the ratio of the predetermined volumetric amount and calibration pressure pulse.

2. A calibrated method for characterizing blood flow as claimed in claim 1 wherein the step of sensing the pressure includes sensing a pressure pulse due to blood flow through the patient's arteries and the step of periodically changing said volume of said blood pressure cuff by a predetermined volumetric amount includes the step of changing said volume based upon a periodic presence of a predetermined plurality of sensed pressure pulses.

3. A calibrated method for characterizing blood flow as claimed in claim 2 wherein the periodic presence of a predetermined plurality of sensed pressure pulses defines a cyclic calibration routine for calculating a plurality of pulsatile blood volumes during the reactive hyperemic episode.

4. A calibrated method for characterizing blood flow as claimed in claim 3 including the step of selecting at least one of said sensed pressure pulses during each cyclic calibration and calculating said pulsatile blood volume based thereon, said step of calculating a plurality of pulsatile blood volumes during the reactive hyperemic episode including the step of utilizing said at least one of said sensed pressure pulses for each said cyclic calibration.

5. A calibrated method for characterizing blood flow as claimed in claim 4 including the step of reducing motion artifacts by averaging one from the group of a predetermined number of sensed pressure pulses in each cyclic calibration and a predetermined number of pulsatile blood volumes in each cyclic calibration.

6. A calibrated method for characterizing blood flow as claimed in claim 4 including the step of correlating an episodic time with each cyclic calibration.

7. A calibrated method for characterizing blood flow as claimed in claim 6 wherein said pulsatile blood volume is a wave and the method includes the step of calculating a plurality of peak values for the pulsatile blood volume during the reactive hyperemic episode.

8. A calibrated method for characterizing blood flow as claimed in claim 7 including the step of graphically presenting said plurality of peak values for the pulsatile blood volume with respect to the correlated episodic time for substantially the entire reactive hyperemic episode.

9. A calibrated method for characterizing blood flow as claimed in claim 8 wherein the step of changing said volume based upon a periodic presence of a predetermined plurality of sensed pressure pulses includes the step of counting sensed pressure pulses.

10. A calibrated method for characterizing blood flow as claimed in claim 9 changing said volume based upon counting a periodic presence of a predetermined plurality of sensed pressure pulses includes the step of counting at least three substantially similar pressure pulses and subsequently changing said volume with said predetermined volumetric amount.

11. A calibrated method for characterizing blood flow as claimed in claim 10 including the step of ignoring a second predetermined plurality of sensed pressure pulses subsequent to changing said volume with said predetermined volumetric amount.

12. A calibrated method for characterizing blood flow as claimed in claim 11 wherein said steps of counting at least three substantially similar pressure pulses, subsequently changing said volume with said predetermined volumetric amount, and ignoring a second predetermined plurality of sensed pressure pulses subsequent to changing said volume defines a cyclic calibration period.

13. A calibrated method for characterizing blood flow as claimed in claim 12 including the step of obtaining said patient's diastolic blood pressure prior to said reactive hyperemic episode and utilizing one of said patient's diastolic pressure and a predetermined, step-down diastolic pressure in the step of establishing said predetermined pressure in said blood pressure cuff during the reactive hyperemic episode.

14. A calibrated method for characterizing blood flow as claimed in claim 13 including the step of occluding blood flow through the limb of said patient for a predetermined time period prior to the step of establishing said predetermined pressure in said blood pressure cuff thereby creating said reactive hyperemic episode in the limb of said patient.

15. A calibrated method for characterizing blood flow as claimed in claim 14 wherein all the steps are noninvasive with respect to said patient and said patient's limb.

16. A calibrated method for characterizing blood flow as claimed in claim 15 including the step of calculating pulsatile blood flow as a volumetric quantity with respect to time.

17. A calibrated method for characterizing blood flow as claimed in claim 15 wherein the step of periodically changing the volume includes one step from the group consisting of adding said predetermined volume and subtracting said predetermined volume to and from said blood pressure cuff.

18. A calibrated method for characterizing blood flow as claimed in claim 8 wherein the step of graphically comparing said plurality of peak values for the pulsatile blood volume with respect to the correlated episodic time includes the step of illustrating said plurality of peak values as a episodic blood volume waveform, and the method includes graphically comparing said episodic blood volume waveform of said patient with a predetermined waveform illustrating a healthy blood volume waveform.

19. A calibrated method for characterizing blood flow as claimed in claim 3 wherein the step of changing said volume based upon a periodic presence of a predetermined plurality of sensed pressure pulses includes the step of counting sensed pressure pulses.

20. A calibrated method for characterizing blood flow as claimed in claim 19 wherein the step of changing said volume based upon counting a periodic presence of a predetermined plurality of sensed pressure pulses includes the step of counting at least three substantially similar pressure pulses and subsequently changing said volume with said predetermined volumetric amount.

21. A calibrated method for characterizing blood flow as claimed in claim 20 including the step of ignoring a second predetermined plurality of sensed pressure pulses subsequent to changing said volume with said predetermined volumetric amount.

22. A calibrated method for characterizing blood flow as claimed in claim 21 wherein said steps of counting at least three substantially similar pressure pulses, subsequently changing said volume with said predetermined volumetric amount, and ignoring a second predetermined plurality of sensed pressure pulses subsequent to changing said volume defines a cyclic calibration period.

23. A calibrated method for characterizing blood flow as claimed in claim 1 wherein the step of periodically changing the volume includes one step from the group consisting of adding said predetermined volume and subtracting said predetermined volume to and from said blood pressure cuff.

24. A calibrated method for determining the condition of blood vessels and endothelium in a limb of a patient during reactive hyperemia with a blood pressure cuff bound about said limb comprising the steps of:
    establishing a predetermined, near diastolic, pressure in said blood pressure cuff during the reactive hyperemic episode;
    substantially continually sensing the pressure in said blood pressure cuff during substantially the entire reactive hyperemic episode;
    periodically changing a volume of said blood pressure cuff by a predetermined volumetric amount and substantially concurrently sensing a resultant change in the pressure as a calibration pressure pulse at a predetermined plurality of calibration cycles during said reactive hyperemic episode;
    determining, for each of said plurality of calibration cycles, a respective peak value for a blood volume, said blood volume obtained by correcting the sensed pressure, at each of said plurality of calibration cycles, with the ratio of the predetermined volumetric amount and calibration pressure pulse obtained during said respective calibration cycle; and
    comparing said peak values for said plurality of calibration cycles with a plurality of predetermined peak blood volume values for healthy blood vessels and endothelium during reactive hyperemia.

25. A calibrated method for determining the condition of blood vessels and endothelium as claimed in claim 24 wherein the step of determining respective peak blood volume values for said plurality of calibration cycles includes the step of correlating the plurality of peak blood volume values for each of said plurality of calibration cycles to an episodic time for said reactive hyperemia.

26. A calibrated method for determining the condition of blood vessels and endothelium as claimed in claim 25 including the step of mapping the episodic correlated plurality of peak blood volume values to said episodic time and wherein said plurality of predetermined peak blood volume values for healthy blood vessels and endothelium is a time-based map including said plurality of predetermined peak blood volume values for healthy blood vessels and endothelium.

27. A calibrated method as claimed in claim 26 wherein said step of continually sensing includes the step of sensing a pressure pulse, and the method includes the step of selecting at least one of said sensed pressure pulses during each calibration cycle and calculating said blood volume based thereon.

28. A calibrated method as claimed in claim 27 including the step of averaging a predetermined number of sensed pressure pulses in each calibration cycle.

29. A calibrated method as claimed in claim 27 wherein the step of changing said volume is based upon detecting a periodic presence of a predetermined plurality of sensed pressure pulses which establishes said calibration cycle and includes the step of counting sensed pressure pulses.

30. A calibrated method as claimed in claim 29 including the step of ignoring a second predetermined plurality of sensed pressure pulses during each calibration cycle subsequent to changing said volume with said predetermined volumetric amount in the same calibration cycle.

31. A calibrated method as claimed in claim 30 including the step of obtaining said patient's diastolic blood pressure prior to said reactive hyperemic episode and utilizing one of said patient's diastolic pressure and a predetermined, step-down diastolic pressure in the step of establishing said predetermined pressure in said blood pressure cuff during the reactive hyperemic episode.

32. A calibrated method as claimed in claim 31 including the step of occluding blood flow through the limb of said patient for a predetermined time period prior to the step of establishing said predetermined pressure in said blood pressure cuff thereby creating said reactive hyperemic episode in the limb of said patient.

33. A calibrated method as claimed in claim 32, including the step of calculating pulsatile blood flow as a volumetric quantity with respect to time.

34. A calibrated method as claimed in claim 33, wherein the step of periodically changing the volume includes one step from the group consisting of adding said predetermined volume and subtracting said predetermined volume to and from said blood pressure cuff.

35. A calibrated method for determining the condition of blood vessels and endothelium as claimed in claim 25 including the step of mapping the episodic correlated plurality of peak blood volume values as a waveform and the method includes the step of graphically displaying the mapped episodic correlated plurality of peak blood volume values as a waveform.

36. A calibrated method for determining the condition of blood vessels and endothelium as claimed in claim 35 including the step of graphically displaying said mapped episodic correlated plurality of peak blood volumes as a waveform substantially simultaneously with a time-based waveform of said plurality of predetermined peak blood volume values for healthy blood vessels and endothelium.

37. A calibrated system for characterizing blood flow in a limb of a patient during reactive hyperemia with a blood pressure cuff bound about said limb comprising:

means, coupled to said blood pressure cuff, for inflating, for a predetermined pre-test time, said blood pressure cuff to a suprasystolic pressure and thereafter establishing a predetermined, near diastolic, pressure in said blood pressure cuff during the ensuing reactive hyperemic episode;

a sensor, pneumatically coupled to said blood pressure cuff, substantially continually sensing the pressure in said cuff and generating a pressure signal during the reactive hyperemic episode;

means, coupled to said blood pressure cuff, for periodically changing a volume of said blood pressure cuff by a predetermined volumetric amount during the reactive hyperemic episode;

means, coupled to said sensor, for generating a calibration pressure pulse signal based upon a resultant change in the pressure signal during the periodic change of volume;

means for calculating a blood volume signal by correcting the sensed pressure signal with a ratio of the predetermined volumetric amount and said calibration pressure pulse signal; and means for quickly releasing said suprasystolic pressure in said blood pressure cuff prior to establishing said predetermined, near diastolic, pressure in said cuff.

38. A calibrated system for characterizing blood flow during reactive hyperemia as claimed in 37 wherein said means for quickly releasing includes an exhaust valve.

39. A calibrated system for characterizing blood flow during reactive hyperemia as claimed in claim 38 wherein said sensor generates pressure pulse signals as part of said pressure signal during said reactive hyperemic episode and the system includes means for counting said pressure pulse signals to establish a calibration cycle.

40. A calibrated system for characterizing blood flow during reactive hyperemia as claimed in claim 39 wherein said reactive hyperemic episode includes a plurality of calibration cycles and the system includes means, coupled to said means for calculating, for correlating said blood volume signal with its respective calibration cycle.

41. A calibrated system for characterizing blood flow during reactive hyperemia as claimed in claim 40 wherein said means for calculating includes means for averaging one of said sensed pressure pulse signals and said blood volume signals in each of said plurality of calibration cycles.

42. A calibrated system for characterizing blood flow during reactive hyperemia as claimed in claim 40 including means, coupled to said means for calculating, for determining pulsatile blood flow as a volumetric quantity with respect to time.

43. A calibrated system for characterizing blood flow during reactive hyperemia as claimed in claim 40 wherein said means for counting is part of means for establishing said calibration cycle, the system including means, coupled to said means for establishing said calibration cycle, for correlating an episodic time of said reactive hyperemic episode with said plurality of calibration cycles.

44. A calibrated system for characterizing blood flow during reactive hyperemia as claimed in claim 43 wherein each said calibration cycle includes a first and a second plurality of pressure pulse signals with said calibration pulse interposed therebetween, said means for calculating said blood volume signal utilizing said first plurality of pressure pulse signals during the respective calibration cycle to calculate said blood volume signal for said respective calibration cycle.

45. A calibrated system for characterizing blood flow during reactive hyperemia as claimed in claim 44 wherein said sensor is noninvasive with respect to said patient's limb and wherein said blood volume signal is a blood volume pulse signal which is based upon said pressure pulse signal.

46. A calibrated system for characterizing blood flow during reactive hyperemia as claimed in claim 45 including means, coupled to said means for calculating, for computing peak blood volume values based upon the blood volume signal for each of said plurality of calibration cycles.

47. A calibrated system for characterizing blood flow during reactive hyperemia as claimed in claim 46 including means, coupled to said means for computing peak blood volume values and said means for correlating an episodic time of said reactive hyperemic episode with said plurality of calibration cycles, for graphically presenting the plurality peak blood volume values with respect to said episodic time was a reactive hyperemic blood flow waveform.

48. A calibrated system for characterizing blood flow during reactive hyperemia as claimed in claim 47 including means for storing a predetermined waveform illustrating a healthy blood flow waveform and the system includes means, coupled to said means for storing and said means for graphically presenting, for graphically comparing and presenting said reactive hyperemic blood flow waveform of said patient with said predetermined waveform illustrating a healthy blood flow.

49. A calibrated system as claimed in claim 48 including means, coupled to said means for calculating, for determining pulsatile blood flow as a volumetric quantity with respect to time.

50. A calibrated system as claimed in claim 49 wherein said means for periodically changing a volume of said blood pressure cuff includes one from the group consisting means for adding said predetermined volumetric amount and means for subtracting said predetermined volumetric amount to and from said blood pressure cuff.

51. A calibrated system for determining the condition of blood vessels and endothelium in a limb of a patient during reactive hyperemia with a blood pressure cuff bound about said limb comprising:

means, coupled to said blood pressure cuff, for inflating, for a predetermined pre-test time, said blood pressure cuff to a suprasystolic pressure and thereafter establishing a predetermined, near diastolic, pressure in said blood pressure cuff during the ensuing reactive hyperemic episode;

a sensor, pneumatically coupled to said blood pressure cuff, substantially continually sensing the pressure in said cuff and generating a pressure signal during the reactive hyperemic episode, said pressure signal including a plurality of pressure pulse signals therein;

means, coupled to said blood pressure cuff, for periodically changing a volume of said blood pressure cuff by a predetermined volumetric amount at a predetermined plurality of calibration cycles during the reactive hyperemic episode;

means, coupled to said sensor and said means for periodically changing volume, for generating a calibration pressure pulse signal during each of said calibration cycles based upon a resultant change in the pressure signal;

means, coupled to said sensor and said means for generating said calibration pulse signal, for determining, for each of said plurality of calibration cycles and during said reactive hyperemic episode, a respective peak value for a blood volume signal, said blood volume signal obtained by correcting the pressure pulse signal, at each of said plurality of calibration cycles, with the ratio of the predetermined volumetric amount and said calibration pressure pulse signal obtained during said respective calibration cycle; and means, coupled to said means for determining, for comparing the peak blood volume values for said plurality of calibration cycles with a plurality of predetermined peak blood volume values for healthy blood vessels and endothelium during reactive hyperemia.

52. A calibrated system for determining the condition of blood vessels and endothelium during reactive hyperemia as claimed in claim 51 wherein the system includes means for monitoring an episodic time for said reactive hyperemia, and the means for determining respective peak blood volume values for said plurality of calibration cycles includes means, coupled to said means for monitoring, for correlating the plurality of peak blood volume values for each of said plurality of calibration cycles to said episodic time for said reactive hyperemia.

53. A calibrated system for determining the condition of blood vessels and endothelium during reactive hyperemia as claimed in claim 52 including means, coupled to said means for correlating, for mapping the episodic correlated plurality of peak blood volume values, and wherein said plurality of predetermined peak blood volume values for healthy blood vessels and endothelium is a time-based map of predetermined blood flow.

54. A calibrated system for determining the condition of blood vessels and endothelium during reactive hyperemia as claimed in claim 53 including means for graphically displaying the mapped episodic correlated plurality of peak blood volume values as a blood flow waveform and a time-based predetermined blood flow waveform for healthy blood vessels and endothelium.

55. A calibrated system for determining the condition of blood vessels and endothelium during reactive hyperemia as claimed in claim 54 including means, coupled to said means for determining, for averaging a predetermined number of pressure pulse signals in each said calibration cycle.

56. A calibrated system for determining the condition of blood vessels and endothelium during reactive hyperemia as claimed in claim 54 wherein said means for changing said volume includes means for counting pressure pulse signals in order to establish said calibration cycle.

57. A calibrated system for determining the condition of blood vessels and endothelium during reactive hyperemia as claimed in claim 56 wherein each said calibration cycle includes a first and a second plurality of pressure pulse signals with said calibration pulse interposed therebetween, said means for determining said blood volume signal utilizing said first plurality of pressure pulse signals during the respective calibration cycle to calculate said blood volume signal for said respective calibration cycle.

58. A calibrated system for determining the condition of blood vessels and endothelium during reactive hyperemia as claimed in claim 57 including means, coupled to said means for determining, for calculating pulsatile blood flow as a volumetric quantity with respect to time.

59. A calibrated system for determining the condition of blood vessels and endothelium during reactive hyperemia as claimed in claim 58 wherein said means for changing the volume includes one from the group consisting means for adding said predetermined volumetric amount and means for subtracting said predetermined volumetric amount to and from said blood pressure cuff.

* * * * *